(12) United States Patent
Agrawal et al.

(10) Patent No.: US 6,600,012 B1
(45) Date of Patent: Jul. 29, 2003

(54) LIPID-MODIFIED MUC-1 DERIVATIVES

(75) Inventors: Babita Agrawal, Edmonton (CA); Mark J. Krantz, Edmonton (CA); Mark A. Reddish, Edmonton (CA); B. Michael Longenecker, Edmonton (CA)

(73) Assignee: Biomira, Inc., Edmonton (CA)

( * ) Notice: Subject to any disclaimer, the term of this patent is extended or adjusted under 35 U.S.C. 154(b) by 0 days.

(21) Appl. No.: 09/497,232

(22) Filed: Feb. 3, 2000

Related U.S. Application Data

(63) Continuation of application No. 09/074,410, filed on May 8, 1998, now abandoned.
(60) Provisional application No. 60/045,949, filed on May 8, 1997.

(51) Int. Cl.$^7$ .......................... C07K 4/00; C07K 14/00
(52) U.S. Cl. ...................... 530/300; 530/324; 530/325; 530/326; 530/327; 530/328
(58) Field of Search ................................. 530/300, 324, 530/325, 326, 327, 328

(56) References Cited

FOREIGN PATENT DOCUMENTS

| WO | WO 95/34628 | 12/1995 |
| WO | WO 95/34638 | 12/1995 |
| WO | WO 96/40066 | 12/1996 |
| WO | WO 98/37095 | 2/1998 |

OTHER PUBLICATIONS

Apostolopoulos et al., 1995 PNAS 92:10128–10132.*
Nair 1993 J of Virology 67 (7) 4063–4069.*
M.A. Alexander et al., "Correlation Between CD8 Dependency and . . . Cytotoxic T Lymphocytes", J. Exp. Med. vol. 173, Apr. 1991, pp. 849–858.
C.R. Alving, "Lipopolysaccharide, Lipid A, and Liposomes Containing Lipid A as Immonlogic Adjuvants", Immunobiol. vol. 187, (1993), pp. 430–446.
F.R. Carbone et al., "Induction of Cytotoxic T Lymphocytes by Primary in vitro Stimulation with Peptides", J. Exp. Med., vol. 167, Jun. 1988, pp. 1767–1779.
M.L.H. DeBruijn et al., "Peptide loading of empty major histocompatibility complex . . . primary cytotoxic T lymphocyte responses", Eur. J. Immunol. 21, (1991). pp. 2963–2970.
M.L.H. DeBruijn et al., "Mechanisms of induction of primary virus–specific cytotoxic T lymphocyte responses", Eur. J. Immunol. 22, (1992), pp. 3013–3020.
C.V. Harding et al., "Liposome–Encapsulated Antigens Engender Lysosomal Processing for Class II MHC . . . Class I Presentation", J. Immun., vol. 147, Nov. 1, 1991, pp. 2860–2863.
J.G.A. Houbiers et al., "In vitro induction of human cytotoxic T lymphocyte responses against peptides of mutant and wild–type p53", Eur. J. Immunol, 23, (1993), pp. 2072–2077.
B.M. Longenecker et al., "Prospects for Mucin Epitopes in Cancer Vaccines", The Immunologist, (1993), pp. 89–93.
S.E. Macatonia et al., "Primary Stimulation by Dendritic Cells Induces Antiviral Proliferative and Cytotoxic T Cell Responses in vitro", J. Exp. Med., vol. 69, Apr. 1989, pp. 1255–1264.
S. Nair et al., "Induction of Primary, Antiviral Cytotoxic, and Proliferative Responses with Antigens Administered via Dendritic Cells", J. Virol., Jul. 1993, pp. 4062–4069.
S. Nair et al., "Soluble Proteins Delivered to Dendritic Cells Via pH–sensitive . . . T Lymphocyte Responses in Vitro", J. Exp. Med., vol. 175, Feb. 1992, pp. 609–612.
S.E. Macatonia et al., "Primary proliferative and cytotoxic T–cell responses to HIV induced in vitro by Human dendritic cells", Immunol., 74, (1991), pp. 399–406.
A. Mehta–Damani et al., "Generation of Antigen–Specific CD8+CTLs from Naive Precursors", J. Immunol., 153, (1994), pp. 996–1003.
H.J. Stauss et al., "Induction of cytotoxic T lymphocytes with peptides in vitro; Identification of candidate T–cell epitopes in human papilloma virus", Proc. Natl. Acad. Sci. Vo. 89, 9/92, pp. 7871–7875.
F. Zhou et al., "Liposome–Mediated Cytoplasmic Delivery . . . Antigen Presentation Pathway", Immuno. (1994), pp. 229–235.
Gagliardi, et al., "Presentation of peptides by cultured monocytes or activated T cells allows specific priming of human cytotoxic T lymphocytes in vitro", International Immunology, vol. 7, No. 11. pp. 1741–1751 (1995).
Agrawal, et al., "In Vitro Induction of MUC–1 Peptide–Specific Type 1 T Lymphocyte and Cyotoxic T Lymphocyte Response from Healthy Multiparous Donors", The Journal of Immunology, XP002078857, 157 (5) pp. 2089–1095, (1996).
Alexander, et al. "Generation of tumor–specific cytolytic T lymphocytes from peripheral blood of cervical cancer patients by in vitro stimulation with a synthetic human papillomavirus type 16 E7 epitope", American Journal of Obstetrics and Gynecology, XP002078856 175 (6) pp 1586–1593, (1996).
B. Agrawal et al., "Does Pregnancy Immunize Against Breast Cancer?", Cancer Res. 55, pp. 2257–2261 Jun. 1, 1995.
B. Agrawal et al., "In Vitro Induction of MUC–1 Peptide–Specific . . . from Healthy Multiparous Donors", J. of Immunology, XP002078857, 157 (5), pp. 2089–2095, 1996.

(List continued on next page.)

*Primary Examiner*—James Housel
*Assistant Examiner*—Myron G. Hill
(74) *Attorney, Agent, or Firm*—Foley & Lardner

(57) ABSTRACT

A method for generating a mixture of activated T-cells by combining a plurality of peripheral blood lymphocytes (PBLs) with an antigen-loaded liposome to produce antigen-loaded PBLs, and combining the antigen-loaded PBLs with a naive, anergic or memory T-cell, to produce an activated T-cell. Such activation is carried out in vivo or in vitro. The antigen-loaded PBLs and activated T-cells, prepared according to the methods of invention, have use as cellular vaccines for treatment of cancer and viral diseases.

16 Claims, 15 Drawing Sheets

OTHER PUBLICATIONS

Alexander et al., "Generation of tumor–specific cytolytic T lymphoctyes . . . type 16 E7 epitope", Am. J. of Obstetrics and Gynecology, XP002078856, 175(6), pp. 1586–1593, 1996.

M. A. Alexander et al., "Correlation Between CD8 Dependency and . . . Cytotoxic T Lymphocytes", J. Exp. Med., vol. 173, pp. 849–858, 1991.

C. R. Alving, "Lipopolysaccharide, Lipid A, and Liposomes Containing Lipid A as Immunologic Adjuvants", Immunobiol., vol. 187, pp. 430–446, 1993.

F. R. Carbone et al., "Induction of Cytotoxic T Lymphocytes by Primary in vitro Stimulation wtih Peptides," J. Exp. Med., vol. 167, pp. 1767–1779, 1988.

M.L.H. DeBruijn et al., "Peptide loading of empty major histocompatibility complex . . . primary cytotoxic . . . Responses", Eur. J. Immunol. 21, pp. 2963–2970, 1991.

M.L.H. DeBruijn et al., "Mechanisms of induction of primary virus specific . . . responses", Eur. J. Immunol. 22, pp. 3013–3020, 1992.

N. Domenech et al., "Identification of an HLA–A1–Restricted Epitope . . . Epithelial Tumor Antigen Mucin", J. Immun., 155, pp. 4766–4774, 1995.

Gagliardi et al., "Presentation of peptides by cultured monocytes or activated T cells . . . in vitro", International Immun., vol. 7:11, pp. 1741–1752, 1995.

C. V. Harding et al., "Liposome–Encapsulated Antigens Engender . . . Class I Presentation", J. Immunol., vol. 147, pp. 2860–2863, 1991.

Houbiers et al., "In vitro induction of human cytotoxic T lymphocytes responses . . . wild–type p53", Eur. J. Immunol., 23, pp. 2072–2077, 1993.

B. M. Longenecker et al., "Prospects for Mucin Epitopes in Cancer Vaccines", Immunogolist, pp. 89–93, 1993.

S. E. Macatonia et al., "Primary Stimulation by Dendritic Cells Induces . . . T Cell Responses in vitro", J. Exp. Med., vol. 69. pp. 1255–1264, 1989.

S. Nair et al., "Induction of Primary, Antiviral Cytotoxic . . . via Dendritic Cells", J. Virol., pp. 4062–4069, 1993.

S. Nair et al., "Soluble Proteins Delivered to Dendritic Cells . . . Responses in Vitro", J. Exp. Med. vol. 175, pp. 609–612, 1992.

S. E. Macatania et al., "Primary proliferative and cytotoxic T–cell responses . . . dendritic cells", Immunol., vol. 74, pp. 399–406, 1991.

A. Mehta–Damani et al., "Generation of Antigen–Specific CD8+CTLs from Naive Precursors", J. Immunol., 153, pp. 996–1003, 1994.

H. J. Strauss et al., "Induction of cytotoxic T lymphocytes with peptides in vitro . . . papilloma virus", Proc. Natl. Acad. Sci., vol. 89, pp. 7871–7875, 1992.

F. Zhou et al., "Liposome–Mediated Cytoplasmic Delivery . . . Antigen Presentation Pathway", Immunol., pp. 229–235, 1994.

F. Zhou et al., "An Improved method of loading pH–sensitive liposomes with soluble . . . antigen presentation", J. of Immuno. Methods, vol. 145, pp. 143–152, 1991.

R. Reddy et al., "pH sensitive liposomes provide an efficient means of sensitizing . . . recognition of a soluble Protein", J. of Immuno Methods, vol. 141, pp. 157–163, 1991.

* cited by examiner

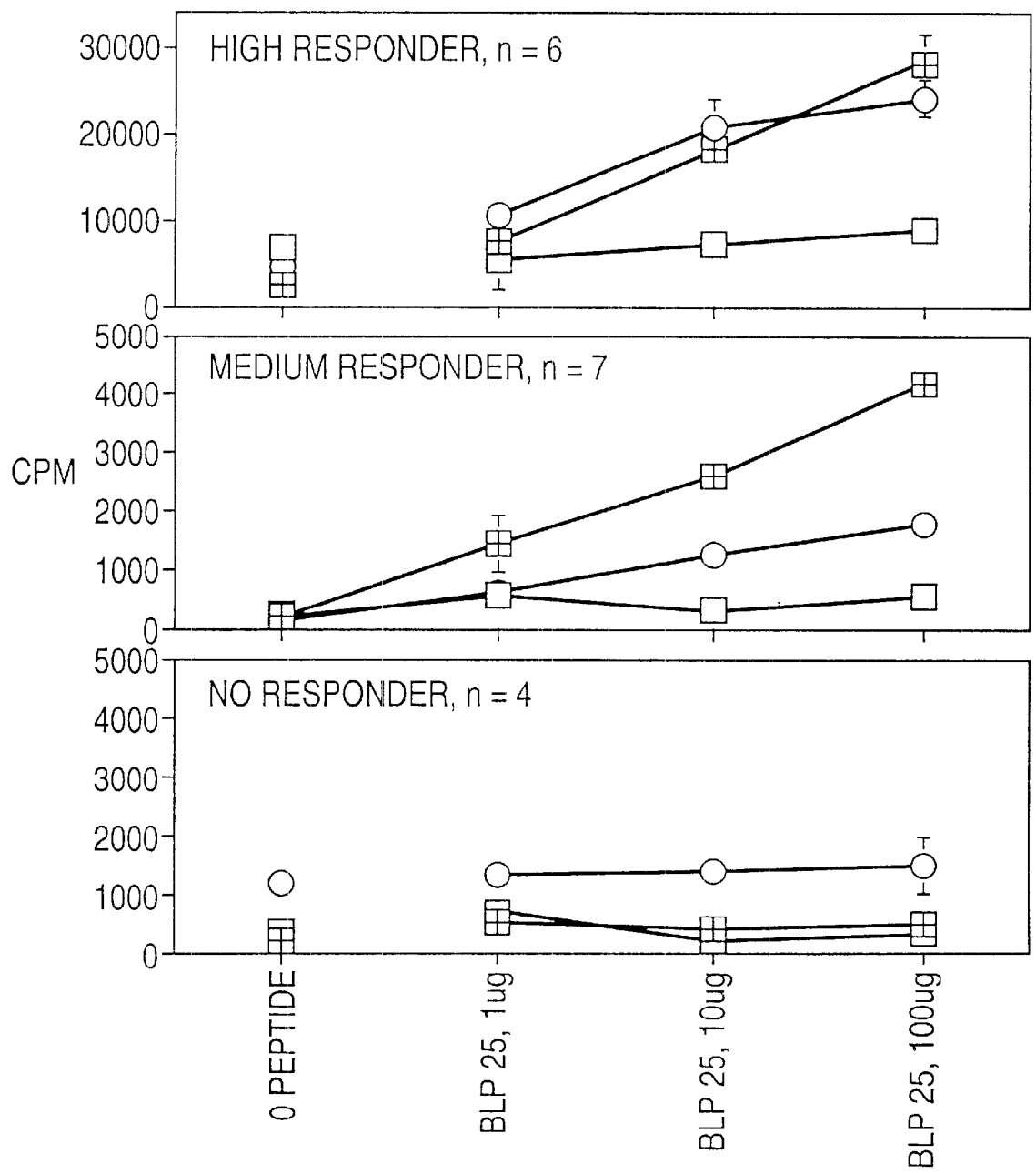

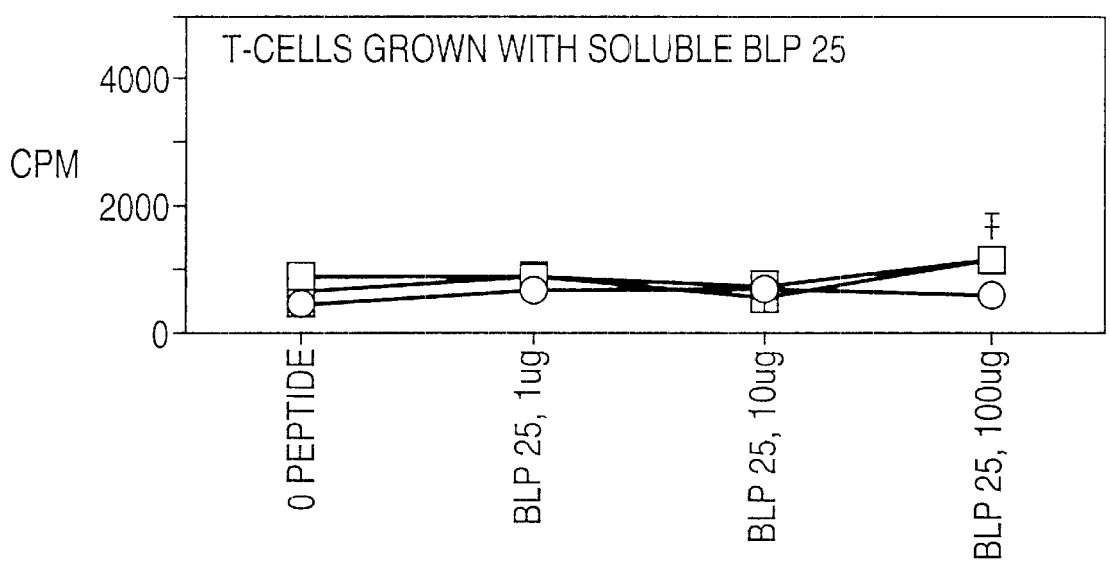

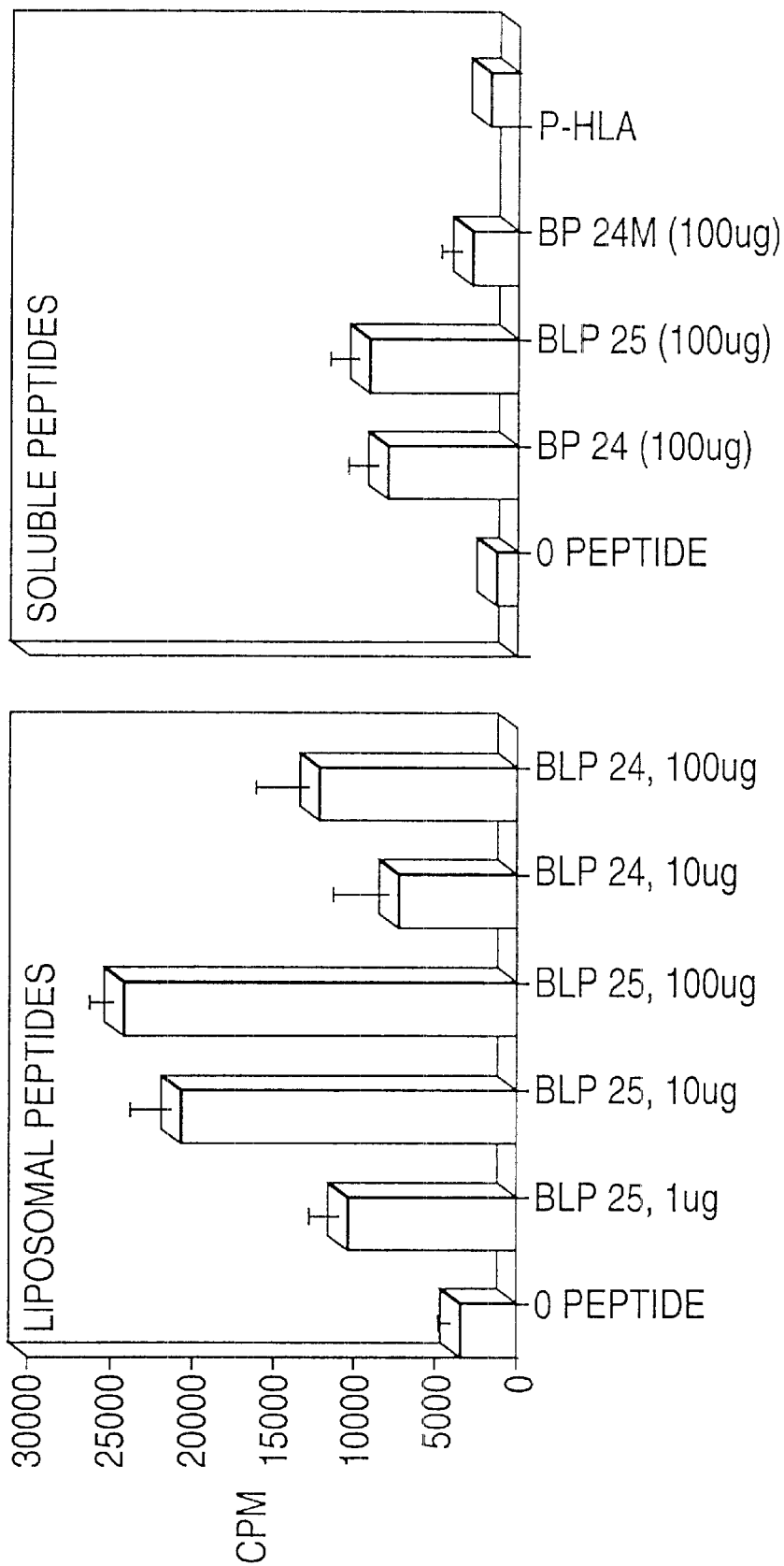

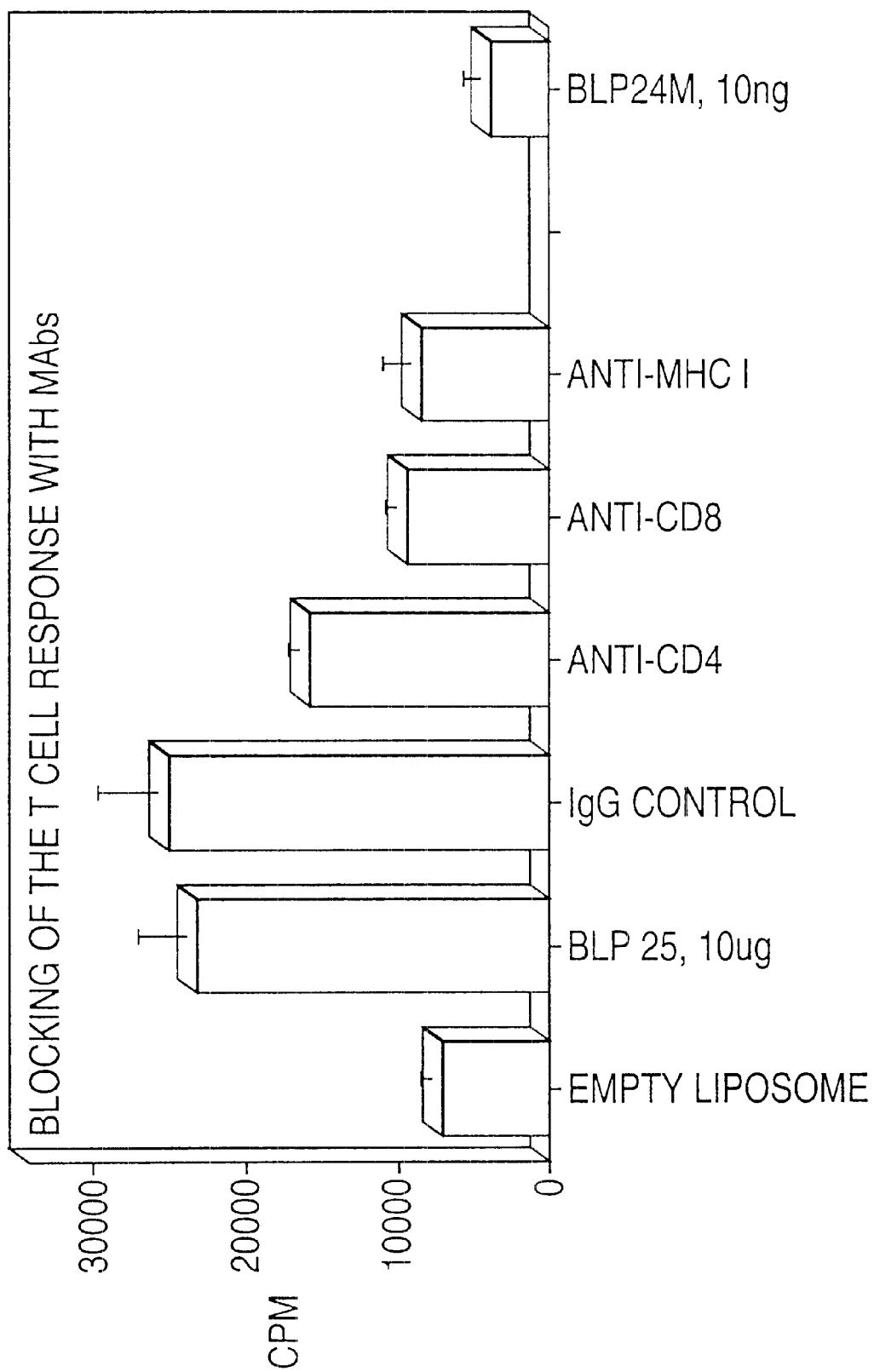

FIG. 6B
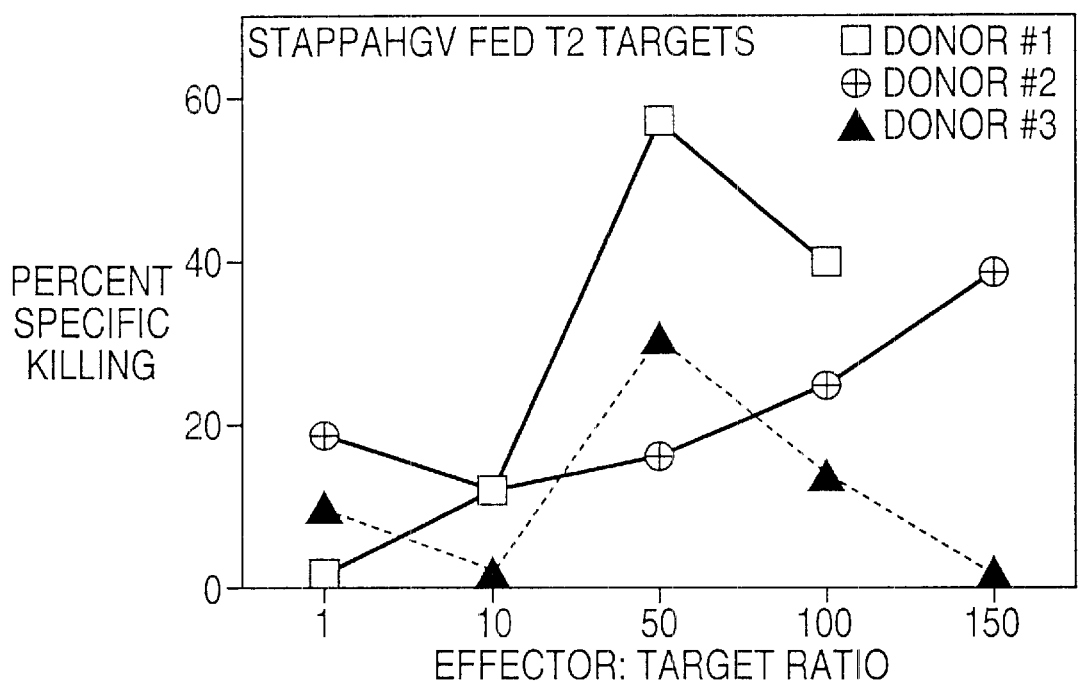
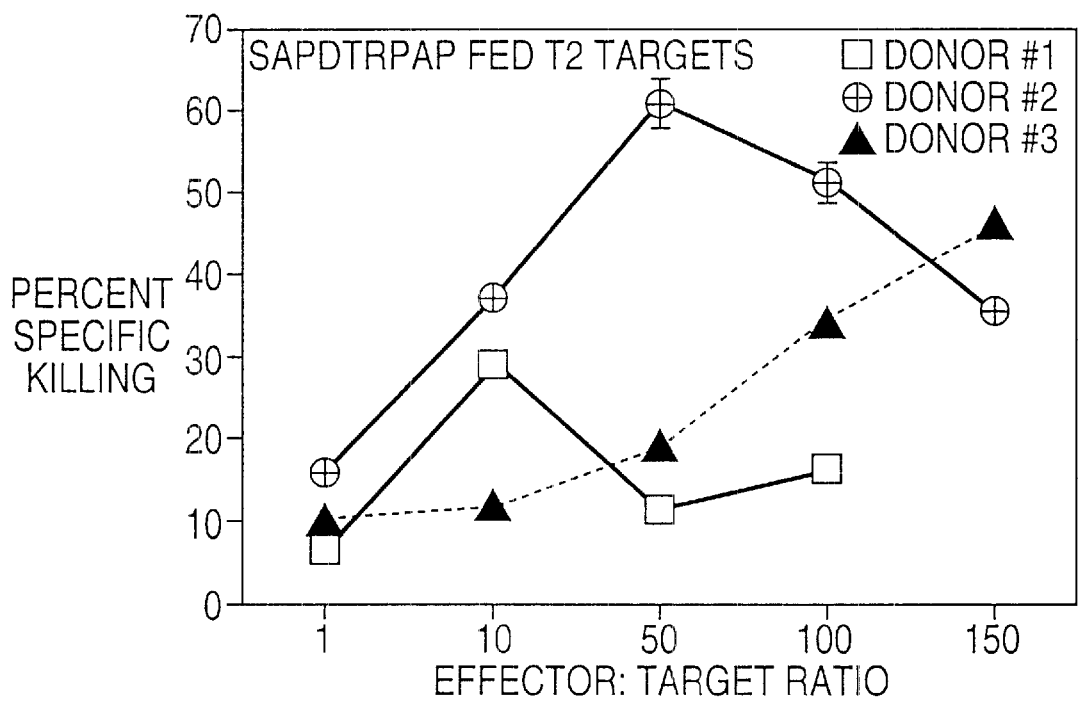

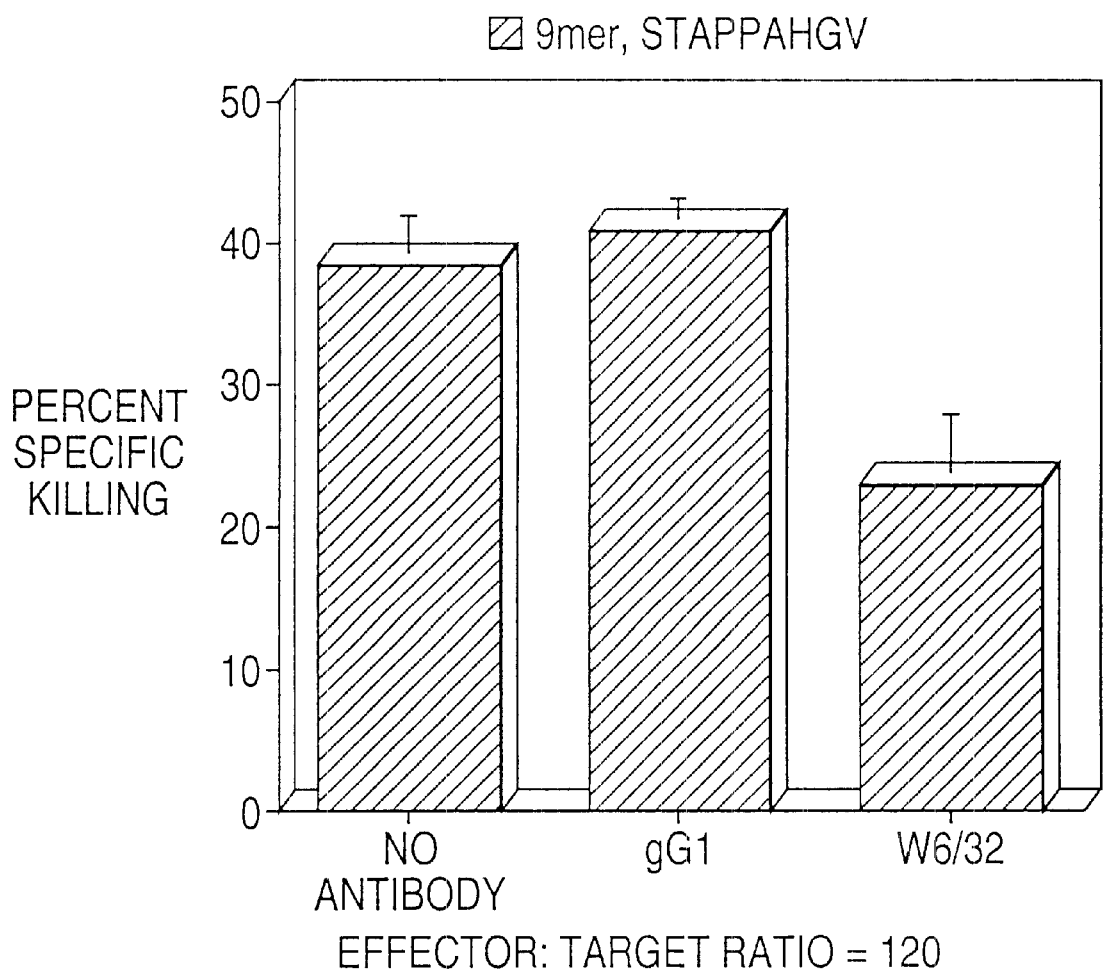

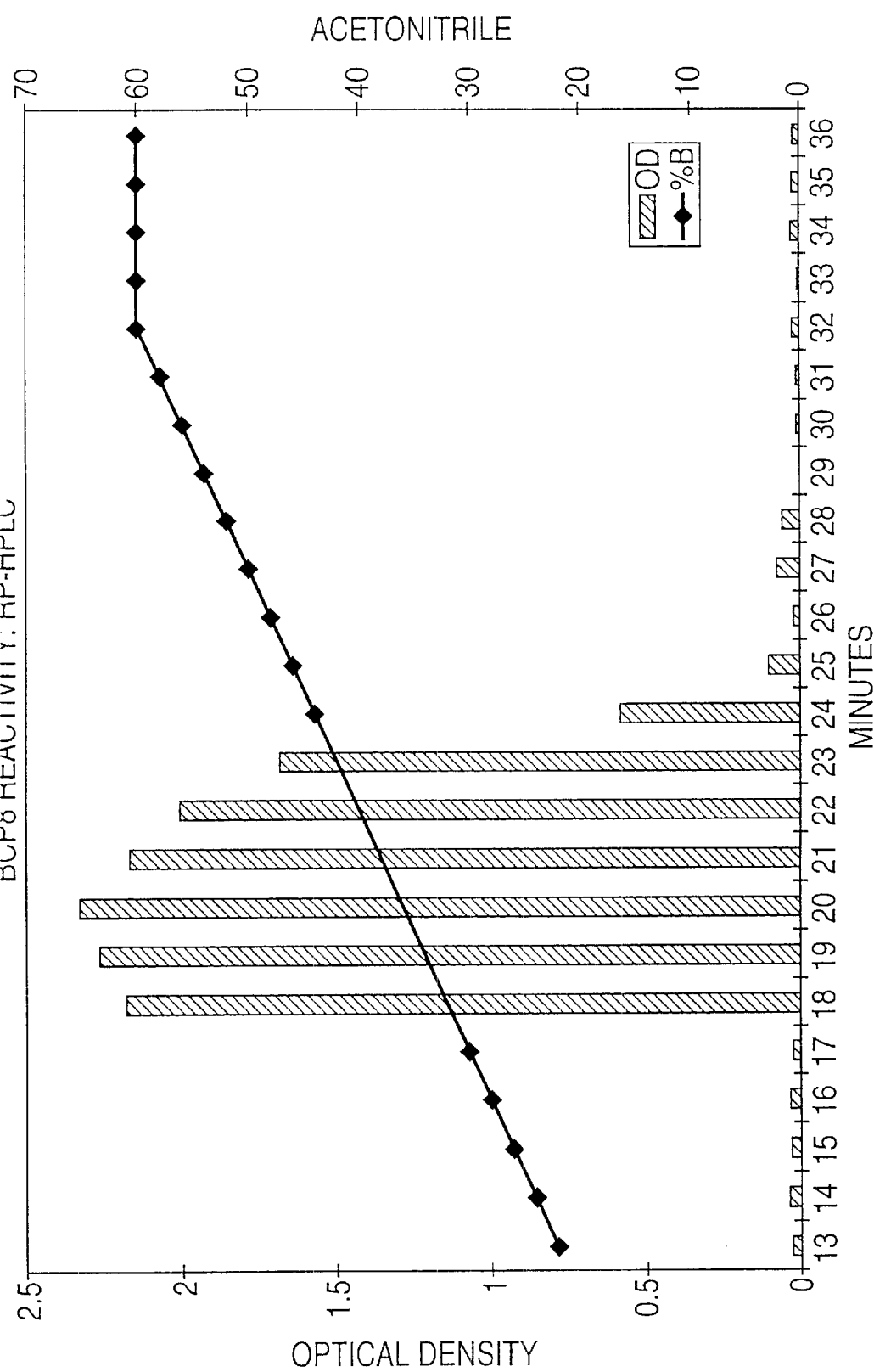

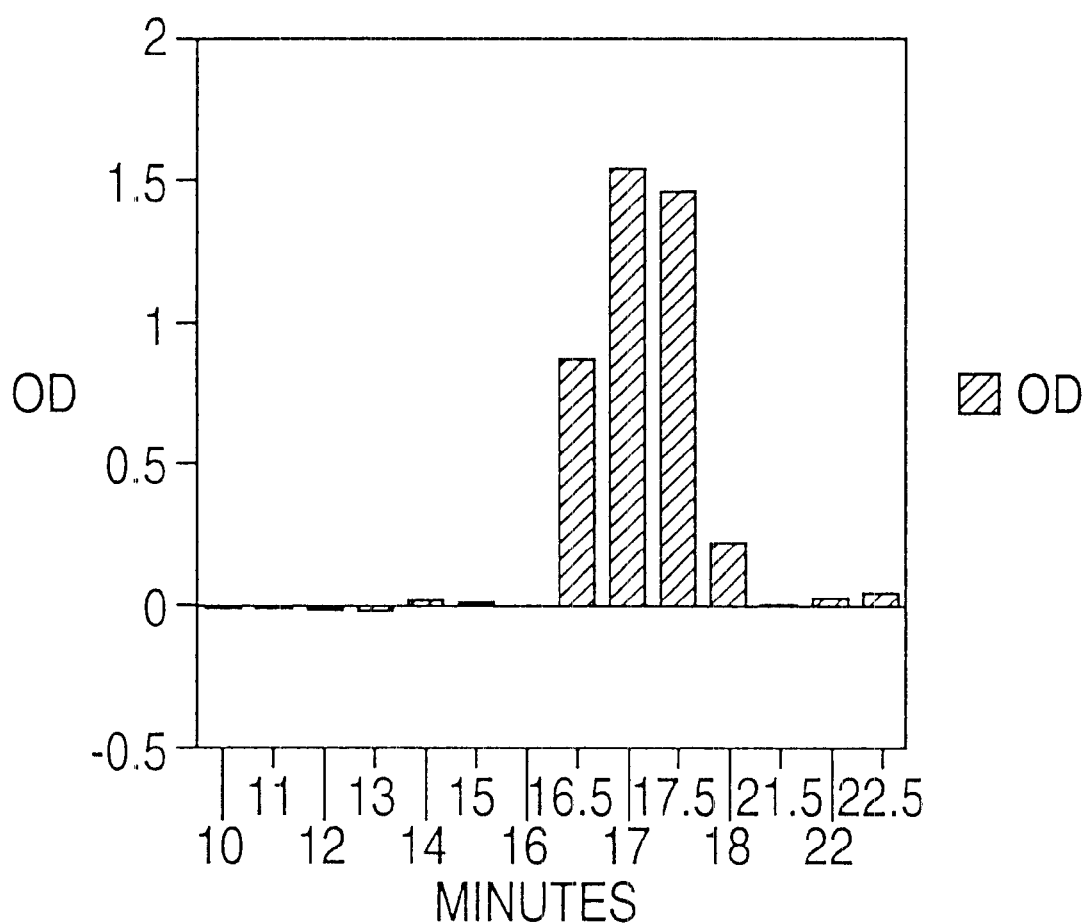

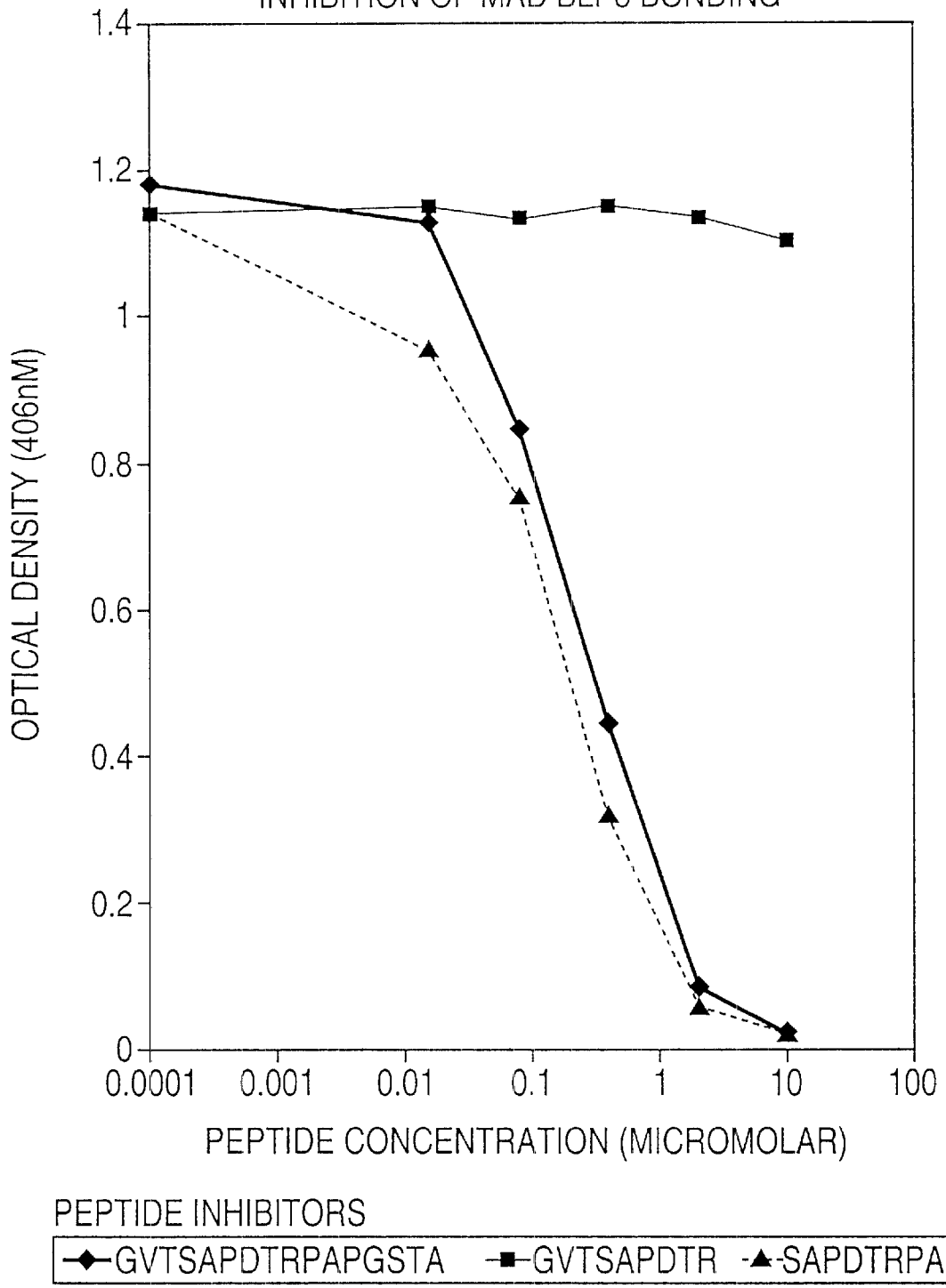

FIG. 11
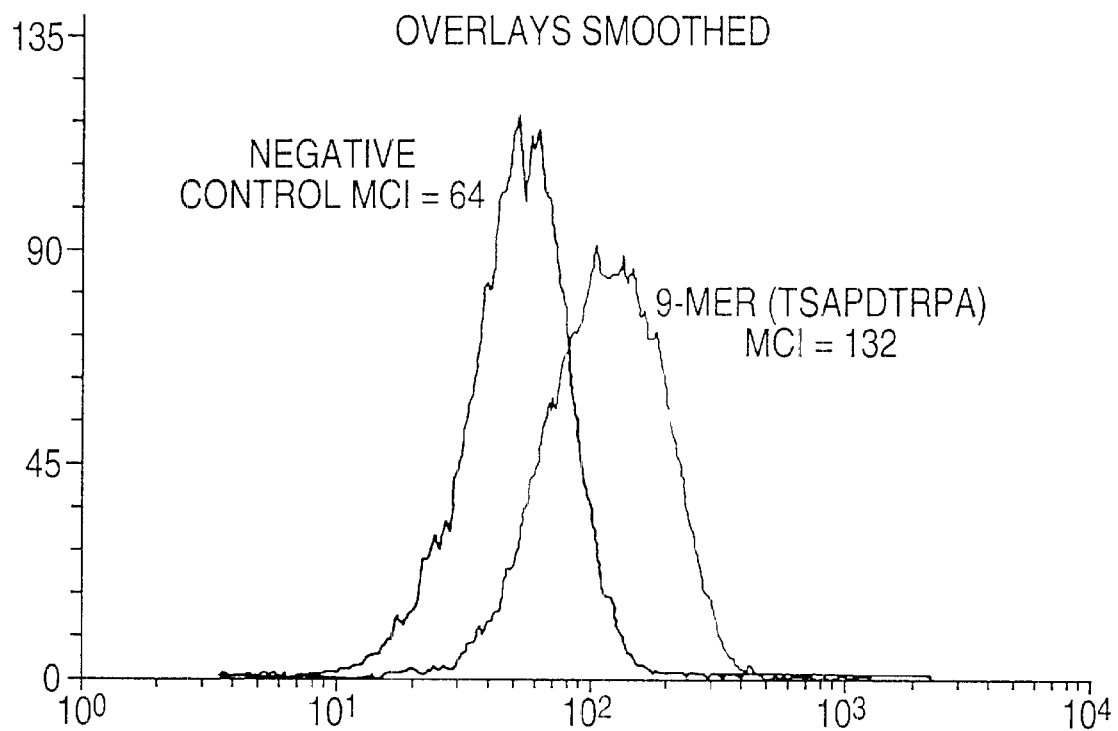
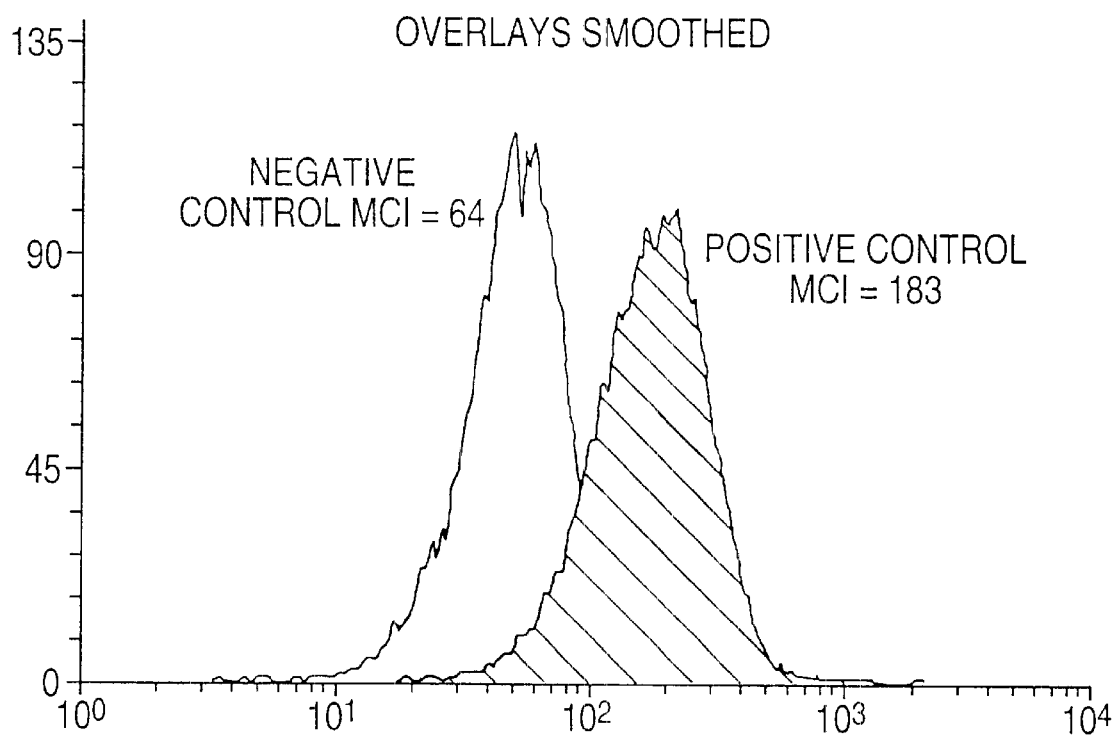

SEQUENCE LISTING (1) GENERAL INFORMATION:

(iii) NUMBER OF SEQUENCES: 34

(2) INFORMATION FOR SEQ ID NO: 1:

(i) SEQUENCE CHARACTERISTICS:
       (A) LENGTH: 9 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 1:

Ser Thr Ala Pro Pro Ala His Gly Val
1               5

(2) INFORMATION FOR SEQ ID NO: 2:

(i) SEQUENCE CHARACTERISTICS:
       (A) LENGTH: 9 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 2:

Ser Ala Pro Asp Thr Arg Pro Ala Pro
1               5

(2) INFORMATION FOR SEQ ID NO: 3:

(i) SEQUENCE CHARACTERISTICS:
       (A) LENGTH: 8 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 3:

Ser Ile Ile Asn Phe Glu Lys Leu
1               5

(2) INFORMATION FOR SEQ ID NO: 4:

(i) SEQUENCE CHARACTERISTICS:
       (A) LENGTH: 10 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 4:

Phe Leu Pro Ser Asp Tyr Phe Pro Ser Val
1               5                   10

(2) INFORMATION FOR SEQ ID NO: 5:

(i) SEQUENCE CHARACTERISTICS:
       (A) LENGTH: 25 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 5:

Ser Thr Ala Pro Pro Ala His Gly Val Thr Ser Ala Pro Asp Thr Arg
1               5                   10                  15
Pro Ala Pro Gly Ser Thr Ala Pro Pro
            20                  25

(2) INFORMATION FOR SEQ ID NO: 6:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 6:

Ser Ala Pro Asp Thr Arg Pro
1               5

(2) INFORMATION FOR SEQ ID NO: 7:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 7:

Asp Thr Arg Pro
1

(2) INFORMATION FOR SEQ ID NO: 8:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 8:

Thr Ser Ala Pro Asp Thr Arg Pro Ala
1               5

(2) INFORMATION FOR SEQ ID NO: 9:

(i) SEQUENCE CHARACTERISTICS:
            (A) LENGTH: 20 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 9:

Pro Asp Thr Arg Pro Ala Pro Gly Ser Thr Ala Pro Pro Ala His Gly
1               5                   10                  15
Val Thr Ser Ala
            20

(2) INFORMATION FOR SEQ ID NO: 10:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 10:

```
Gly Val Thr Ser Ala Pro Asp Thr Arg Pro Ala Pro Gly Ser Thr Ala
1               5                   10                  15
Pro Pro Ala His
            20
```

(2) INFORMATION FOR SEQ ID NO: 11:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 11:

```
Thr Ser Ala Pro Asp Thr Arg Pro Ala Pro Gly Ser Thr Ala Pro Pro
1               5                   10                  15
Ala His Gly Val
            20
```

(2) INFORMATION FOR SEQ ID NO: 12:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 12:

```
Gly Val Thr Ser
1
```

(2) INFORMATION FOR SEQ ID NO: 13:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 13:

```
Thr Ser Ala Pro
1
```

(2) INFORMATION FOR SEQ ID NO: 14:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 14:

Pro Asp Thr Arg
1

(2) INFORMATION FOR SEQ ID NO: 15:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 15:

Gly Val Thr Ser Ala Pro Asp Thr Arg Pro Ala Pro Gly Ser Thr Ala
1               5                   10                  15

(2) INFORMATION FOR SEQ ID NO: 16:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 16:

Thr Ser Ala Pro Asp Thr Arg
1               5

(2) INFORMATION FOR SEQ ID NO: 17:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 17:

Gly Val Thr Ser Ala Pro Asp Thr Arg
1               5

(2) INFORMATION FOR SEQ ID NO: 18:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 18:

Val Thr Ser Ala Pro Asp Thr Arg Pro
1               5

(2) INFORMATION FOR SEQ ID NO: 19:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 19:

Ala Pro Asp Thr Arg Pro Ala Pro Gly
1               5

(2) INFORMATION FOR SEQ ID NO: 20:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 20:

Pro Asp Thr Arg Pro Ala Pro Gly Ser
1               5

(2) INFORMATION FOR SEQ ID NO: 21:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 21:

Asp Thr Arg Pro Ala Pro Gly Ser Thr
1               5

(2) INFORMATION FOR SEQ ID NO: 22:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 22:

Glu Ala Glu Glu Ala Ala Arg Leu Gln Ala
1               5                   10

(2) INFORMATION FOR SEQ ID NO: 23:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 23:

Thr Ala Pro Pro Ala His Gly Val Thr Ser Ala Pro Asp Thr Arg Pro
1               5                   10                  15

Ala Pro Gly Ser Thr Ala Pro Pro
            20

(2) INFORMATION FOR SEQ ID NO: 24:

(i) SEQUENCE CHARACTERISTICS:
        (A) LENGTH: 24 amino acids (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 24:

Asp Ser Thr Ser Ser Pro Val His Ser Gly Thr Ser Ser Pro Ala Thr
1               5                   10                  15

Ser Ala Pro Glu Asp Ser Thr Ser
            20

(2) INFORMATION FOR SEQ ID NO: 25:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 25:

Ala Thr Ala Pro Pro Ala His Gly Val
1               5

(2) INFORMATION FOR SEQ ID NO: 26:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 26:

Gly Val Thr Ser Ala Pro Asp Thr Arg Pro
1               5                   10

(2) INFORMATION FOR SEQ ID NO: 27:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 27:

Val Thr Ser Ala Pro Asp Thr Arg Pro Ala
1               5                   10

(2) INFORMATION FOR SEQ ID NO: 28:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 28:

Thr Ser Ala Pro Asp Thr Arg Pro Ala Pro
1               5                   10

(2) INFORMATION FOR SEQ ID NO: 29:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 29:

Ser Ala Pro Asp Thr Arg Pro Ala Pro Gly
1               5                   10

(2) INFORMATION FOR SEQ ID NO: 30:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 30:

Ala Pro Asp Thr Arg Pro Ala Pro Gly Ser
1               5                   10

(2) INFORMATION FOR SEQ ID NO: 31:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 31:

Pro Asp Thr Arg Pro Ala Pro Gly Ser Thr
1               5                   10

(2) INFORMATION FOR SEQ ID NO: 32:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 32:

Pro Asp Thr Arg Pro Ala
1               5

(2) INFORMATION FOR SEQ ID NO: 33:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 33:

Thr Ser Ala Pro Asp Thr
1               5

(2) INFORMATION FOR SEQ ID NO: 34:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 34:

```
Asn Ala Asn Pro Asn Ala Asn Pro Asn Ala Asn Pro
1               5                   10
```

LIPID-MODIFIED MUC-1 DERIVATIVES

This application is a continuation of U.S. application Ser. No. 09/074,410, filed May 8, 1998, now abandoned which claims the benefit of U.S. Provisional Application No. 60/045,949 filed May 8, 1997.

BACKGROUND OF THE INVENTION

Antigen-specific major histocompatibility complex (MHC)-restricted T-cell responses are an important component of immune responses against viral infections and tumors. Design and development of immunotherapy intervention depends upon understanding the target antigen as well as its capability to be efficiently presented to T-cells along with MHC class I and class II molecules.

With modern techniques, it is possible to determine the affinity of target antigen peptide to the antigen binding groove of MHC class I and class II molecules. However, it lo is not an easy task to predict the immunogenicity of a given antigenic peptide in the outbred human population, given our varying T-cell repertoires. The complexity is further increased with certain tumor antigens which are often recognized as "self" peptides. Thus, a gene encoding a tumor antigen will be expressed in normal autologous cells without any change in nucleotide sequence.

Many adenocarcinomas, such as breast, ovarian, pancreatic, and colorectal, are highly expressed on the cell surface and secrete abnormal (underglycosylated) MUC-1 mucin. As a result of underglycosylation, MUC-1 mucin on these adenocarcinomas has exposed peptide epitopes. Hull, et al., (1989) *Cancer Commun.* 1:261–267; Burchell et al., (1987) *Cancer Res.* 47:5476–5482. This contrasts with normal ductal epithelium cells, where MUC-1 mucin is expressed on the apical surface and has a peptide core of a conserved tandem repeat of 20 amino acid units that is highly glycosylated and therefore has a hidden (cryptic) peptide core. In this normal situation, it is believed that the antigenic regions of MUC-1 are immunologically shielded.

Peptide epitopes on the tandem repeat regions of the MUC-1 mucin peptide core have been recognized as potential target antigens for immunotherapy of certain adenocarcinomas. Gendler et al., (1988) *J. Biol. Chem.* 263:12820–12823; Siddiqui et al., (1988) *Proc. Natl. Acad. Sci. U.S.A.* 85:2320–2323; Longenecker, et al., (1993) *Immunologists.* 1:89–95. It has been demonstrated that MUC-1 peptide specific T-cells have the potential to kill MUC-1 mucin bearing tumor cells. Agrawal et al., (1996) *J. Immunol.* 156:2089–2095. The following permissive peptide epitopes have also been defined: (1) epitope of the MUC-1 peptide-core for class II restricted $CD4^+$ T-cell response and (2) an epitope which has the capability to bind to HLA.A11, HLA.A2.1, HLA.A3 and HLA.A1 Agrawal et al., (1995) *Cancer Res.* 55:2257–2261; Domenech et al., (1995) *J. Immunol.* 155:4766–4774. The usefulness of these peptides as potential vaccine candidates for the inmmunotherapy of various cancers depends upon their ability to generate strong $CD4^+$ and $CD8^+$ T-cell responses. It is generally feasible to determine the immunogenicity of a target peptide in mice after in vivo priming.

It has been reported (Agrawal et al., J. Immunol. and Agrawal et al., *Cancer Res., supra*) that MUC-1 antigen peptide specific $CD4^+$ and $CD8^+$ T-cells were isolated from PBLs obtained from healthy multiparous donors but not from nulliparous women or from men. However, in those studies, subjects were primed in vivo, and isolated T-cells were stimulated in vitro with soluble MUC-1 antigen peptide as antigen.

Recent research suggests that a primary $CD8^+$ cytotoxic T-cell lymphocyte (CTL) response can be generated in vitro by stimulation of T-cells with mutant T2 or RMA-S cell lines that were treated, or "loaded," with peptide. DeBruijn et al., (1992) *Eur. J. Immunol.* 21:2963–2970; DeBruijn et al., (1992) *Eur. J. Immunol.* 22:3013–3020; Stauss et al., (1992) *Proc. Natl. Acad. Sci. U.S.A.* 89:7871–7875; Houbiers et al., (1993) *Eur. J. Immunol.* 23:2072–2077. As used in this specification, a liposome that has been "loaded" with peptide is a formulated product with either membrane-associated and/or intravesicular peptide antigen. Such a "loaded liposome" is used as a delivery vehicle to "load" cells with peptide antigen. Thus, a "loaded cell" is one that has effectively received, or taken up, peptide antigen. A loaded antigen-presenting cell (APC) is one that has taken up peptide antigen and expresses the antigen at the cell surface in the context of MHC class I or class II molecules. In addition, it was shown that antigen specific CTL could be generated in vitro using murine spleen cells having a high concentration of exogenous peptide. Alexander et al., (1991) *J. Exp. Med.* 173:849–858; Carbone et al., (1988) *J. Exp. Med.* 167:1767–1779.

Exogenously provided soluble peptides generally go through the endo-lysosomal presentation pathway for presentation in context of MHC class II molecules. Townsend et al., (1989) *Annu. Rev. Imununol.* 7:601–624; Unanue et al., (1987) *Science* 236:551–557. pH insensitive liposomes were shown to sensitize the APCs for class II restricted presentation. Furthermore, it has been shown that at high concentration of encapsulated antigen peptide, a pH insensitive liposome can deliver antigen to both endocytic and cytoplasmic locations for presentation by both MHC class I and MHC class II molecules. Harding et al., (1991) *J. Immunol.* 147:2860–2863; Zhou et al., (1994) *Immunomethods* 4:229–235.

PBLs pulsed with soluble peptides have been shown to be incapable of inducing primary T-cells in vitro. Germain et al., (1993) *Annu. Rev. Immunol.* 11:403–450. It was also shown that liposome encapsulated antigen was efficiently presented by DC but not macrophages to stimulate primary CTLs. Nair et al., (1993) *J. Virol,* 67:4062–4069. The purification and isolation of dendritic cells (DCs) is however, a difficult task and requires a large number of PBLs or bone marrow stem cells.

Dendritic cells were initially considered to be potential APCs to prime naive T-cells. Steinman, (1991) *Annu. Rev. Immunol.* 9:271–296. Dendritic cells have been used as APCs for in vitro stimulation of primary antigen-specific CTL responses (DeBrujin et al., *Eur. J. Immunol.* 22, supra, Nair et al., supra); Macatonia et al., (1989) *J. Exp. Med.* 169:1255–1264; Macatonia et al., (1991) *Immunology.* 74:399–406; Mehta-Damani et al., (1994) *J. Immunol.* 153:996–1003; Nair et al., (1992) *J. Exp. Med.* 175:609–612. It has been suggested that DCs are capable of intensive aggregation with unprimed T-cells and express a high density of accessory molecules, such as B7.1 and B7.2. Such accessory molecules are critical for stimulation of naive resting T-cells (Steinman, supra). B7.1 is one the "second signal" receptors referred to as co-stimulatory molecules. It is the ligand for CD28 and is critical for the induction of $T_H1$ responses. B7.2 is also a CD28 ligand and is associated with $T_H2$ responsiveness. Also included in the category of co-stimulatory molecules is ICAM-1, which is the natural ligand of LFA, but is also shown to bind to MUC-1. Reginbald et al., (1996) *Cancer Res.* 56:4244.

However, DCs are not good candidates for (1) determining the immunogenicity of various peptides for immunotherapy and (2) stimulation of T-cells for expansion for adoptive cell therapy. In this regard, the prior art relates to generation of antigen-specific CD8+ CTL responses using DCs. The prior art does not suggest how to generate antigen-specific CD4+ CTL responses. The skilled artisan will recognize that CD4+ cytotoxic T-cells exist that will via class II-restricted peptide presentation. In addition the art does not suggest how to generate a mixture of antigen-specific T-cells that are CD8+ (T-cytotoxic) and CD4+ (T-helper).

SUMMARY OF THE INVENTION

The present invention provides a method for generating activated T-cells, comprising:
  (a) combining liposome-encapsulated peptide antigen with a plurality of peripheral blood lymphocytes to produce antigen-loaded antigen-presenting cells;
  (b) combining naive or anergic T-cells with said antigen-loaded antigen-presenting cells;
  (c) isolating activated T-cells from the combination of step (b).

In a further embodiment, the present invention provides such a method wherein said activated T-cells are T helper cells and provides a method wherein said activated T-cells are cytotoxic T-cells.

In a still further embodiment, the invention provides such a method, wherein said liposome comprises monophosphoryl lipid A.

In yet another embodiment, the invention provides such a method, wherein said peptide antigen is BLP-25.

The invention also includes such a method wherein the combination of step (b) comprises IL-7 and IL-12.

The invention further includes such a method wherein said activated T-cell comprises a CD4 receptor and a method wherein said activated T-cell comprises a CD8 receptor.

In yet another embodiment; the invention comprises such a method wherein said activated T-cell is antigen-specific.

In other embodiments, the invention comprises such a method, wherein said antigen is MUC-1, or wherein said antigen is BLP-25.

In another embodiment, the present invention provides a method for producing a cellular vaccine, comprising combining liposome-encapsulated peptide antigen with a plurality of peripheral blood lymphocytes to produce antigen-loaded antigen-presenting cells, which comprise a cellular vaccine.

The present invention also provides a method for treating a patient suffering from cancer, comprising treating said patient with a pharmaceutically effective amount of a cellular vaccine, wherein said vaccine is produced by combining a plurality of peripheral blood lymphocytes with liposome-encapsulated peptide antigen to produce antigen-loaded antigen-presenting cells.

BRIEF DESCRIPTION OF THE DRAWINGS

FIG. 1: Proliferative response of T-cells from peripheral blood lymphocytes of various normal donors towards liposome encapsulated antigen BLP-25.

T-cell response from a total of 17 donors were categorized into (1A) high, (1B) medium and (1C) no responders. The proliferation assay was done according to materials and methods. The T-cells were grown in presence or autologous APCs loaded with liposomes containing BLP-25 at 1 µg □, 10 µg ○ and 100 µg ⊠.

FIG. 2: Representative experiment from T-cell proliferative response from three high responder normal donors. These T-cells were grown in presence of soluble peptide BLP-25 and autologous APCs. The T-cell proliferative response was determined against soluble peptide in presence of autologous APCs. The T-cells were grown in presence of 1 µg □, 10 µg ○ and 100 µg ⊠ of BLP-25 and autologous APCs.

FIG. 3: Antigen specificity of the T-cells stimulated with liposomal BLP-25 loaded autologous APCs. The T-cells isolated from PBLs of normal donors were cultured in presence of autologous PBLs loaded with liposomes containing BLP-25 (10 µg) for two weeks (as stated in materials and methods). These T-cells were tested for their proliferative response against (3A) liposomal antigen peptide or (3B) soluble peptide loaded autologous APCs. As an irrelevant antigen control, 24 amino acid peptide from HLA.Aw68.1 (residue 61–84) was used in soluble form.

FIG. 4: Blocking of antigen peptide specific T-cell proliferative response by MAbs specific against CD4, CD8 and MHC class I molecules. All of the blocking Mabs and isotype control antibody were used at a concentration of 20 µg/ml. The T-cells were cultured in presence of autologous APCs loaded with BLP-25 (10 µg) for two weeks as stated in material and methods and proliferative response was examined against autologous APCs loaded with BLP-25 (10 µg) with or without antibodies or with control peptide BLP-24M containing liposomes loaded APCs.

Figure 5A:
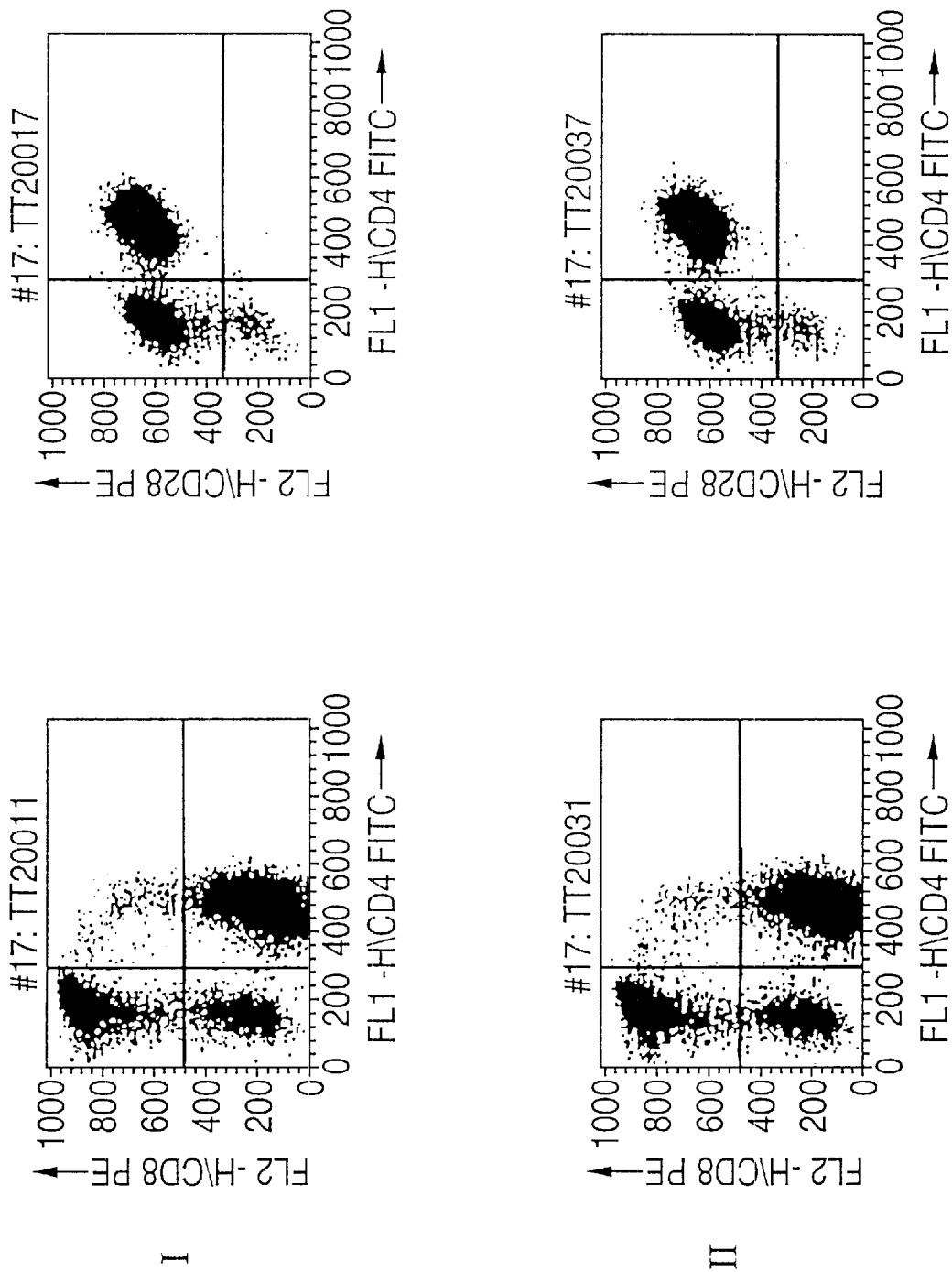

FIG. 5A: The phenotype of T-cells cultured with liposomal BLP-25 (10 µg) loaded on autologous APCs. Presence of both CD4+ and CD8+ T-cells was observed. All of the T-cells were CD28+. The upper (I) and lower (II) panels represent data from cultured T-cells from two different donors.

Figure 5B:
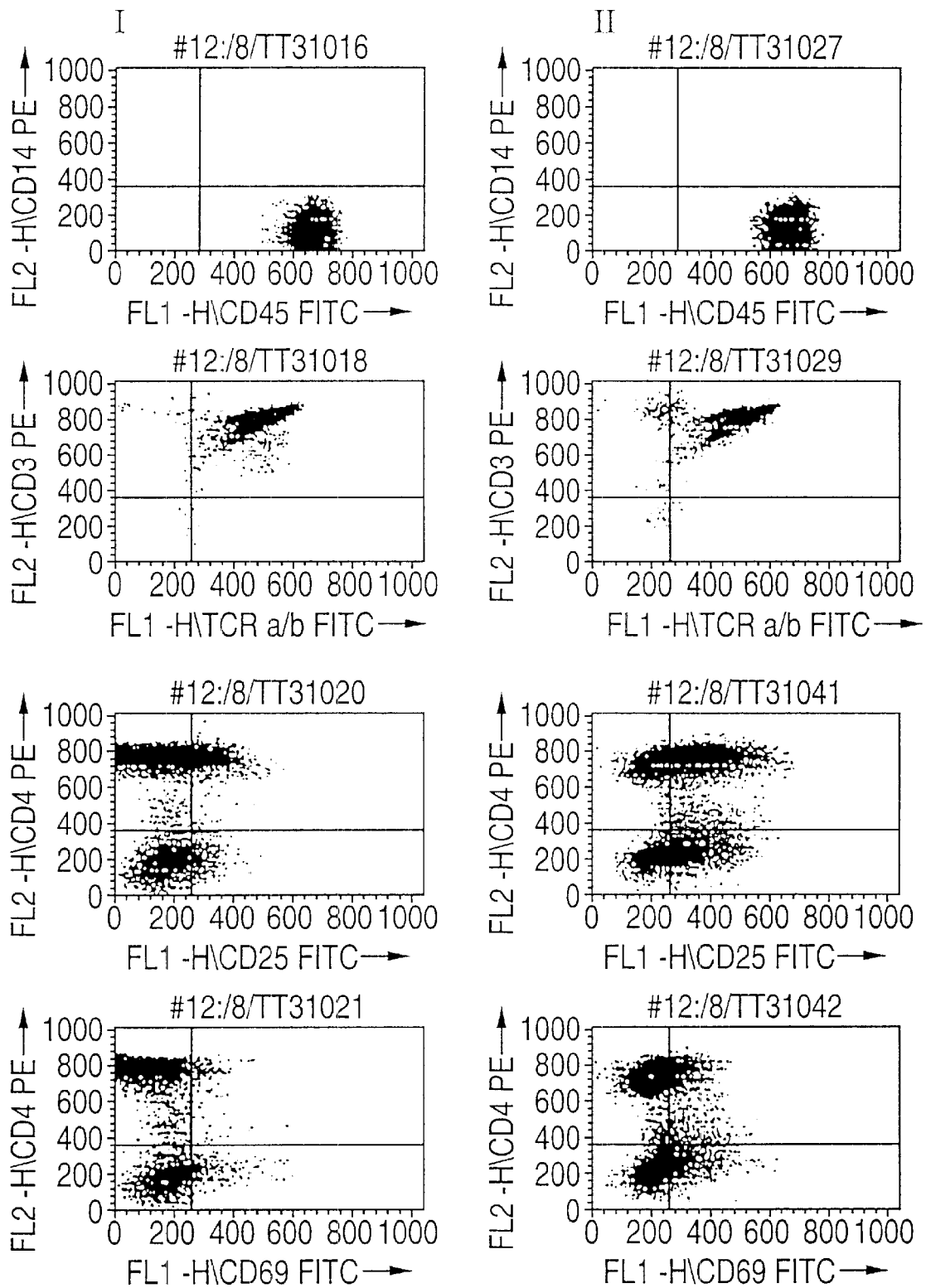

FIG. 5B: The phenotype (TCR and activation molecules) of T-cells cultured in the presence of autologous APCs containing empty liposomes (Left Panel I, no antigen) or BLP-25 (10 µg) containing liposomes (Right Panel II). The higher percentages of CD25+ and CD69+ T-cells in Panel II compared to Panel I represent antigen specific stimulation of these T-cells.

The markers in all of the dot blot graphs are set in a way so as to exclude >98% of isotype control antibody stained cells, treated in a similar manner (isotype control data not shown). The leukogate (CD14/CD45) and TCR (CD3/αβ) staining was performed to ensure the identity of the cultured cells.

Figure 6A:
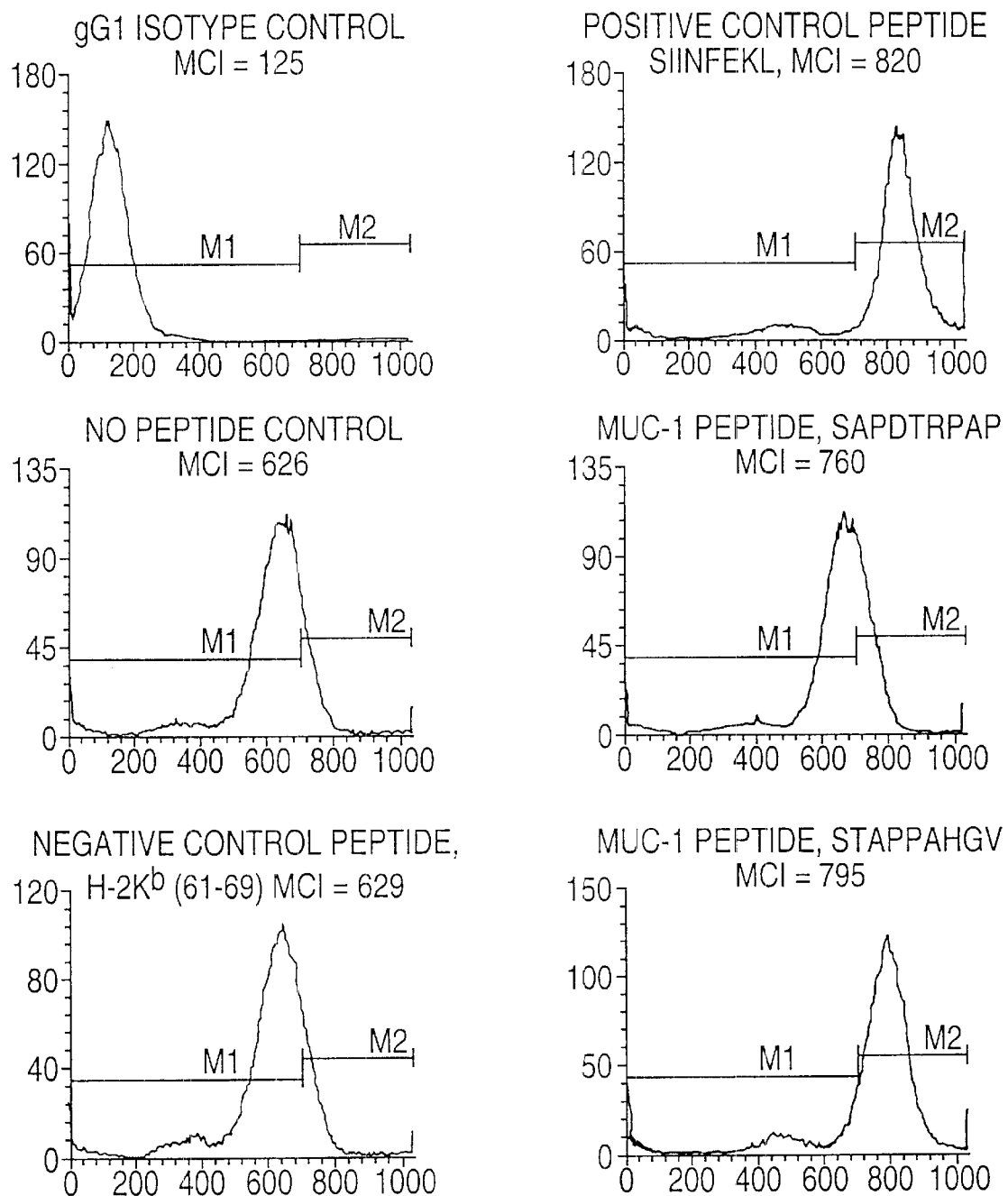

FIG. 6A: Upregulation of HLA.A2 expression on T2 mutant cells by MUC-1 peptides STAPPAHGV (SEQ ID NO: 1) and SAPDTRPAP (SEQ ID NO: 2). SIINFEKL was used as a positive control (SEQ ID NO: 1) and H-2Kb (61–69) peptide (SEQ ID NO: 3) was used as negative control for HLA-A2 upregulation. The x-axis represents fluorescence intensity and the y-axis represents the cell number. Markers M1 and M2 were set to visually examine the increase expression of HLA.A2. Mean channel intensity (MCI) is shown in each histogram.

FIG. 6B: The cytotoxic activity of T-cells cultured with liposomal BLP-2L 25 (10 µg) loaded on autologous APCs. All three donors were HLA.A2+. The targets were T2 cells loaded with the indicated peptides (SEQ ID NOS: 1 & 2, respectively). The 51Cr release from negative control (SEQ ID NO: 3), SIINFEKL-loaded T2 cells has been subtracted from each data point.

FIG. 6C: Anti-HLA class I MAb (W6/32) inhibits killing by T-cells (from donor #2) of (SEQ ID NO: 1) STAPPAHGV-loaded T2 cells. This blocking experiment was performed on donors #1 and #3 with similar results. The isotype control antibody was at the same concentration as W6/32.

FIG. 7: Primary RP-HPLC chromatogram showing 18–22 min elution, BCP8 reactivity as detected by coating diluted fractions on solid phases. Bound BCP8 MAb was detected via GαM $I_gG_{2b}$HRP based ELISA. MCF-7 derived HLA class I molecules (W6/32 purified) were acid eluted and subjected to RP-HPLC using a ZORBAX C8 matrix.

FIG. 8: Results of secondary Zorbax C8 RP-HPLC of the 17 min peak identified as BCP8 reactive in FIG. 1. Strong BCP8 reactivity at 16–19 min on secondary RP-HPLC of pooled BCP8 positive fractions.

FIG. 9: Inhibition of binding of BCP8 to the isolated peptides by (synthetic MUC-1 peptides (SEQ ID NOS 15, 17 and 2, respectively).

Figure 10:
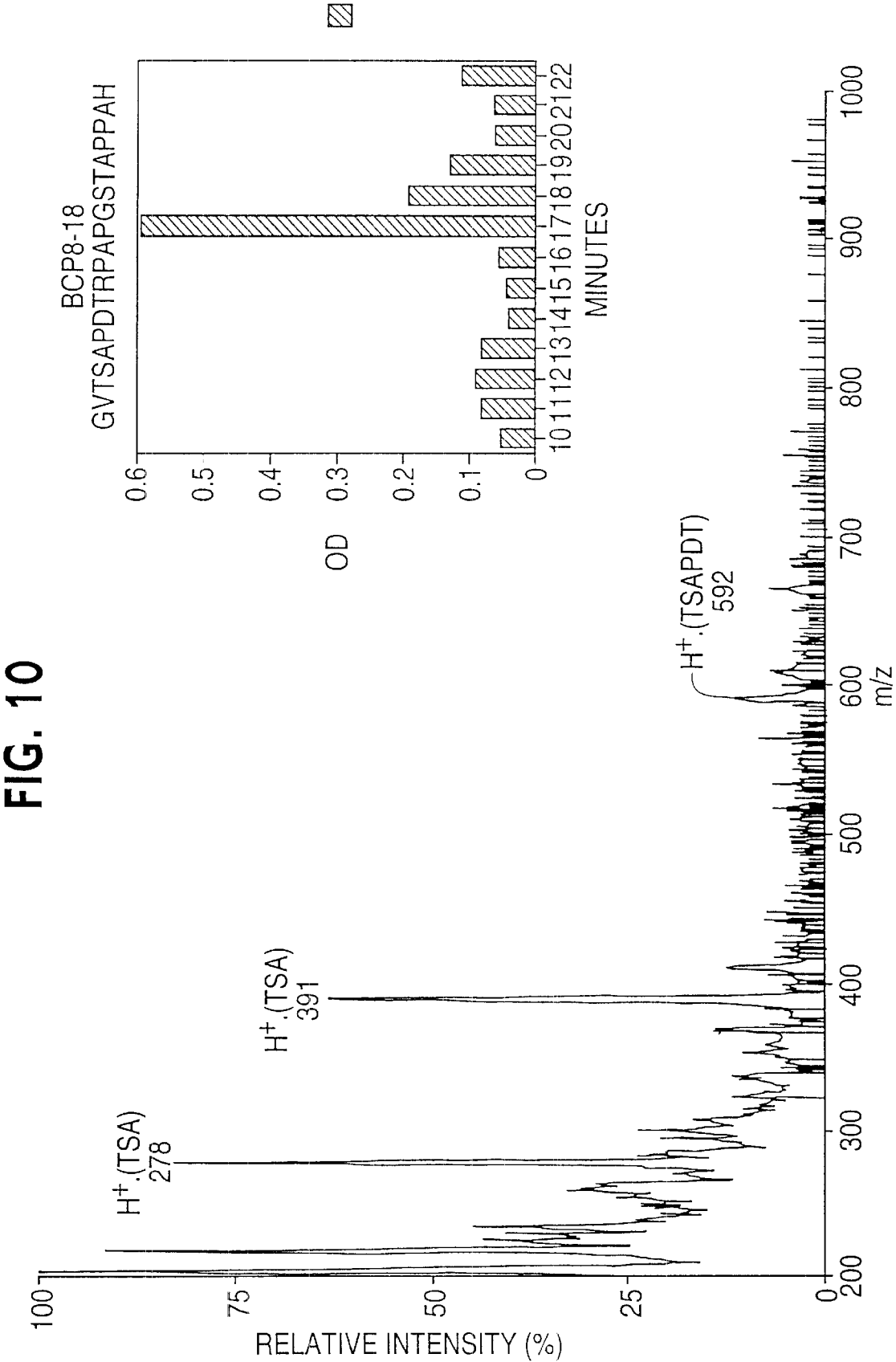

FIG. 10: The sample was obtained by BCP8 affinity isolation of the 17–19 min peak obtained from the secondary RP-HPLC. The affinity isolated peptides were acid eluted from BCP8 and rechromatographed on ZORBAX C8. Electrospray mass spectrum showing three fragments (SEQ ID NO: 33), eluted from MHC class I proteins, presumed to be the degradation products of a longer sequence (SEQ ID NO: 10), during the acid elution. These fragments (SEQ ID NO: 33) were the only ones related to MUC-1 mucin (from sequence data, not shown) while others were of unknown origin.

FIG. 11: Change in mean channel intensity (δMCI) (=$MCI_{(sample)}$−$MCI_{(unfed\ control)}$) of the fluorescence measured on T2 cells with the monoclonal antibody MA2.1 (anti-HLA.A2.1), in an indirect staining procedure. $3 \times 10^5$ T2 cells were cultured overnight with 40 μmoles of synthetic 9 mer (SEQ ID NO: 8) or 10 mer from the MUC-1 tandem repeat, in the presence of 20 μg/ml of β2-microglobulin. Positive control peptide (SEQ ID NO: 4) FLPSDYFPSV δMCI=951.3. FLPSDYFPSV (SEQ ID NO: 4) are also shown.

Figure 12:
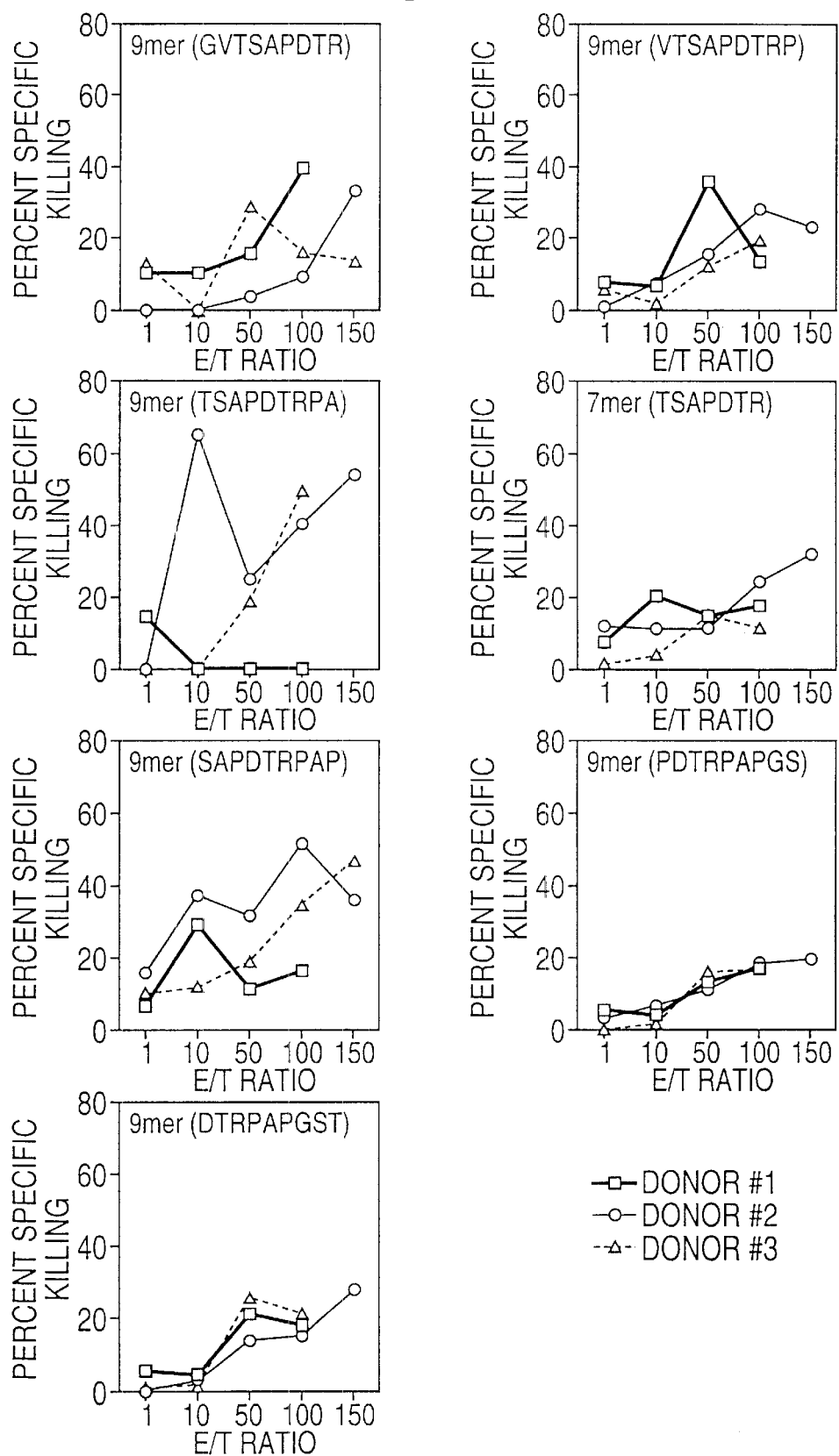

FIG. 12: Cytotoxic activity of MUC-1 peptide stimulated T-cells (SEQ ID NOS 2, 8, 16, 17, 18, 20 and 21). The data are shown with three HLA.A2+ donors.

DETAILED DESCRIPTION

The present invention relates to the generation of activated T-cells. Different embodiments involve generating activated cells from using (a) naive or anergic T-cells or mixtures of both, (b) liposome-encapsulated antigen, and (c) autologous whole peripheral blood lymphocytes (PBLs) as antigen presenting cells.

In a preferred embodiment the invention relates to the production of a population of MUC-1 peptide specific, activated CD4+ and CD8+ T-cells, which are generated in vitro by activating naive T-cells with PBLs (as APCs) that were previously loaded with liposome encapsulated peptide antigens. Typically, the resultant antigen specific CD4+ and CD8+ T-cells have surface molecules associated with activated T-cells and produce a high concentration of γ-IFN and moderate concentration of IL-10 in the culture but only trace amounts of IL-4.

As used in this specification, an "activated T-cell" is one that is in the following phases of the cell cycle: the $G_1$ phase, the S phase, the $G_2$ phase or the M (mitosis) phase. Thus, an "activated T-cell" is undergoing mitosis and/or cell division. An activated T-cell may be a T helper ($T_H$) cell or a cytotoxic T-cell (cytotoxic T lymphocyte (CTL or $T_C$)). Activation of a naive T-cell may be initiated by exposure of such a cell to an APC (which contains antigen/MHC complexes) and to a molecule such as IL-1, IL-2, IL-12, IL-13, γ-IFN, and similar lymphokines. The antigen/MHC complex interacts with a receptor on the surface of the T-cell (T-cell receptor (TCR)). Golub et al., eds. Immunology: a Synthesis, Chapter 2: "The T-cell Receptor" (1991).

As used in this specification, "priming" is used to mean exposing an animal (including a human) or cultured cells to antigen, in a manner that results in activation and/or memory. The generation of CD4+ and CD8+ T-cell responses against a target antigen is usually dependent upon in vivo priming, either through natural infection or through deliberate immunization.

As used in this specification, a "naive" T-cell is one that has not been exposed to foreign antigen (non-autologous) antigen or one that has not been exposed to cryptic autologous antigen. A "naive" T-cell is sometimes referred to as an "unprimed" T-cell. The skilled artisan will recognize that a "resting" cell is in the $G_0$ phase of the cell cycle and hence is not dividing or undergoing mitosis. The skilled artisan will also recognize that an "anergic" T-cell is one that is unable to function properly; i.e., such as a cell that lacks the ability to mediate the normal immune response. T-cells from diseased patients may contain T-cells that have been primed, but are anergic.

The skilled artisan will recognize that suitable accessory molecules may also be used for activation of T-cells. An accessory molecule is a molecule which facilitates the antigen-MHC interaction with the T-cell receptor. Accessory molecules have a variety of roles, including, but not limited to facilitating or enhancing initial binding, stabilizing binding, signal transduction and separation. Examples of such accessory molecules include, but are not limited to, B7.1 (binds to CD28); B7.2 (binds to CD28); and ICAM-1 (binds to LFA-1).

In another embodiment, the invention relates to the generation of activated T-cells using naive T-cells, memory T-cells, and anergic T-cells, or a mixture of all three cell types, along with liposome-encapsulated antigen and autologous whole peripheral blood lymphocytes (PBLs) as antigen presenting cells. As used in this specification "memory T-cells," also known as "memory phenotype" T-cells, is used to designate a class of T-cells that have previously encountered a peptide antigen but are now resting and are capable of being activated. Memory T-cells are T-cells which have been exposed to antigen and then survive for extended periods in the body without the presence of stimulating antigen. However, these memory T-cells respond to "recall" antigens.

In general, memory T-cells are more responsive to a "recall" antigen, when compared with the naive T-cell response to peptide antigen. Memory cells can be recognized by the presence of certain cell-surface antigens, such as CD45R0, CD58, CD11α, CD29, CD44 and CD26, which are markers for differentiated T-cells.

Memory T-cells are isolated by techniques well-known to the skilled artisan. Briefly, the total T-cell population is isolated, followed by fluorescence activated cell sorting (FACS) using anti-CD45R0, anti-CD44 or anti-CD26 monoclonal antibodies. See Hollsberg et al., (1993) *Cellular Immunology* 149:170; Bruno et al., (1995) *Immunity* 2(1):37; and (1993) *Journal of Immunology* 150 (part 1):3119.

A. Antigens

1. Generally Useful Antigens

Antigen specific MHC class II and class I restricted CD4+ and CD8+ T-cell responses are important host immune responses against a variety of pathogenic conditions. Of particular interest, therefore, is the generation of an antigen specific T-cell response. As used in this specification, an "antigen specific" T-cell response is a T-cell response (proliferative, cytotoxic, cytokine secretion) to a given antigenic stimulus, such as a peptide, which is not evident with other stimuli, such as peptides with different amino acid sequences (control peptides). The responsiveness of the T-cell is measured by assessing the appearance of cell surface molecules that are characteristic of T-cell activation, including, but not limited to CD25 and CD69. Such assays are known in the art.

The present methods apply generally to a great variety of antigens. These antigens may be of nearly any chemical constitution, as long as they are able to elicit a T-cell-specific immune response; they may contain at least one T-cell-specific epitope. Exemplary antigens can be derived from peptides, carbohydrates, lipids and especially combinations thereof. Particularly important antigens are peptides, lipopeptides and glycopeptides. Idiotypic and antiidiotypic antigens are specifically included.

Antigens against which it would be highly advantageous to use the subject methods include tumor antigens. Tumor antigens are usually native or foreign antigens which are correlated with the presence of a tumor. Inasmuch as tumor antigens are useful in differentiating abnormal from normal tissue, they are useful not only in diagnosis, but also as a target for therapeutic intervention. Thus, the use of the present methods to generate a T-cell-specific immune response against tumor antigens is an important aspect of the invention.

Tumor antigens are well known in the art. Indeed, several examples are well-characterized and are currently the focus of great interest in the generation of tumor-specific therapies. Non-limiting examples of tumor antigens are carcinoembryonic antigen (CEA), prostate specific antigen (PSA), melanoma antigens (MAGE, BAGE, GAGE), and mucins, such as MUC-1.

MUC-1 mucin antigen has been recognized as a potential immunotherapy target to generate immunity against a number of adenocarcinomas. Longenecker et al., (1993) *Immunologists* 1:89. Thus, one embodiment of the invention relates to a "MUC-1 derivative" which is capable of binding to either or both class I and class II molecules on the surface of an APC.

"MUC-1 derivatives" are typically peptides or peptide-based. In one embodiment, this peptide comprises a core tandem repeat of MUC-1. In yet another embodiment, the invention relates to a 25 amino acid peptide from this core region having the sequence: STAPPAHGVTSAPDTRAPG-STAPP. This core region may also be modified, as described in detail below, in ways which the derivative retains the characteristic of T-cell activation.

A MUC-1 derivative may be a fragment of the MUC-1 protein. Such fragments may be glycosylated or unglycosylated. In accordance with the present invention, fragments within the invention can be obtained from purified MUC-1 or MUC-1 produced by recombinant DNA methodology, using methods that include digestion with proteases, such as pepsin or papain. Of course, MUC-1 fragments also may be made directly by recombinant methods. In addition, MUC-1 fragments encompassed by the present invention can be synthesized using an automated peptide synthesizer such as those supplied commercially by Applied Biosystems, Multiple Peptide Systems and others, or they may be produced manually, using techniques well known in the art. See Geysen et al., *J. Immunol. Methods* 102: 259 (1978).

MUC-1 derivatives also include glycosylated or non-glycosylated synthetic peptides. In addition, MUC-1 derivatives within the present invention include proteolytic cleavage-resistant MUC-1 fragments or MUC-1 fragments containing one or more non-natural amino acids, such as D-amino acids. It is expected that such derivatives would obtain the benefit of increased circulating half-life, while retaining the beneficial T-cell specificity.

In another embodiment, the MUC-1 derivative would include a portion of the extracellular tandem repeat region of MUC-1, with the amino acid sequence DTR (Asp-Thr-Arg) or (SEQ ID NO: 7) DTRP (Asp-Thr-Arg-Pro). Preferably this includes the sequence (SEQ ID NO: 6) SAPDTRP (Ser-Ala-Pro-Asp-Thr-Arg-Pro). A particularly preferred peptide is (SEQ ID NO: 8) TSAPDTRPA.

Some preferred MUC-1 derivatives consist essentially of one peptide core repeat of the MUC-1 mucin. A MUC-1 peptide core repeat in the native MUC-1 molecule comprises the 20 amino acid sequence (SEQ ID NO: 9) PDTRPAPG-STAPPAHGVTSA (Pro-Asp-Arg-Thr-Pro-Ala-Pro-Gly-Ser-Thr-Ala-Pro-Pro-Ala-His-Gly-Val-Thr-Ser-Ala). Useful synthetic derivatives include "linear permutations" of this sequence, for example, (SEQ ID NO: 10) GVTSAPDTR-PAPGSTAPPAH or TSAPDTRPAPGSTAPPAHGV, where the repeat merely begins with GVTS or TSAP, rather than PDTR. The other, analogous permutations are also possible.

Moreover, one or more amino acids of the core sequence may be altered, preferably in a conservative manner known in the art, such that the requisite T-cell-activating activity is maintained. Typical substitutions may be made among the following groups of amino acids: (a) G, A, V, L and I; (b) G and P; (c) S, C, T, M; (d) F, Y, and W; (e) H, K and R; and (f) D, E, N, and Q. Some preferred substitutions may be made among the following groups: (i) S and T; (ii) P and G; a (iii) A, V, L and I.

Other MUC-1 derivatives consist essentially of one truncated peptide core repeat of the MUC-1 mucin, for example, (SEQ ID NO: 1 5) GVTSAPDTRPAPGSTA. Of course this truncated core sequence may be permuted and otherwise altered as described above.

Some embodiments contemplate multimers of core repeats and derivatives thereof (as described above). Multimers can contain multiple copies of the same core repeat or derivative, or they can be mixed and matched. These multimers, although not strictly limited in size, will usually lose their immunostimulatory characteristics, and in fact may cause immunosuppression, with increasing numbers of repeats. It is, therefore, preferable that the number of repeats used be less than three. Some preferred MUC-1 derivative comprise from one to three copies of a 7–20 amino acid long peptide derived from the MUC-1 core peptide, STAPPAH-GVTSAPDTRPAPGSTAPP (SEQ ID NO: 5).

As described above, these preferred MUC-1 derivatives may be glycosylated or partially glycosylated according to methods known in the art. Moreover, it is contemplated that MUC-1 and MUC-1 derivatives can be modified with large molecular weight polymers, such as polyethylene glycols. In addition, lipid modifications are preferred because they may facilitate the encapsulation or interaction of the derivative with liposomes. Exemplary lipid moieties useful for this purpose include, but are not limited to, palmitoyl, myristoyl, stearoyl and decanoyl groups or, more generally, any $C_2$ to $C_{30}$ saturated, monounsaturated or polyunsaturated fatty acyl group.

For convenience in making chemical modifications, it is sometimes useful to include in a MUC-1 peptide one or more amino acids having a side chain amenable to modification. A preferred amino acid is lysine, which may readily be modified at the $\epsilon$-amino group. Side chain carboxyls of aspartate and glutamate are readily modified, as are serine, threonine and tyrosine hydroxyl groups, the cystine sulfhydryl group and the histidine amino group.

Also illustrative of an MUC-1 derivative within the present invention is a non-peptide "mimetic," i.e., a compound that mimics one or more functional characteristics of the MUC-1 protein. Mimetics are generally water-soluble, resistant to proteolysis, and non-immunogenic. Conformationally restricted, cyclic organic peptides which mimic MUC-1 can be produced in accordance with known methods described, for example, by Saragovi, et al., *Science* 253: 792 (1991).

"MUC-1 carbohydrate derivatives" are also contemplated. Such a derivative, as used herein, refers to a glycopeptide which retains the immunostimulatory characteristic of MUC-1 derivatives. Such a carbohydrate derivative may include all or part of the carbohydrate that is attached to the MUC-1 protein. Mimetics that mimic at least one property of MUC-1 carbohydrate may also be used.

The skilled artisan will recognize that other antigens may be used for the generation of activated T-cells. Examples of such antigens include, but are not limited to, non-self (foreign) peptide antigens, and peptide antigens from a virus, tumor, bacterium or other parasite.

2. Identification of Other Useful Antigens

While whole antigens useful in the present methods may be identified using recognized methodologies for measuring various T-cell responses, it is of interest to generate a more specific response, associated with a particular epitope. This approach allows the use of much smaller, and thus more economically produced, antigenic stimuli. Hence, preferred antigens are small molecules, typically peptides or peptide derivatives on the order of less than about 100 amino acids and usually less than about 60 amino acids.

According to methods known in the art, once a native (large) antigen has been identified, its antigenicity can be further refined to one or a few specific epitopes. One classic method involves proteolytic treatment of the large antigen to derive smaller antigens. In addition, fragments of protein antigens can be produced by recombinant DNA techniques and assayed to identify particular epitopes. Moreover, small peptides can be produced by in vitro synthetic methods and assayed.

As an alternative to the random approach of making parts of the intact antigen then assaying them, a more biologically relevant approach is possible. Specifically, since antigenic fragments which bind to MHC class I and/or class II molecules are of particular importance, one exemplary approach is to isolate the MHC molecules themselves and then to isolate the peptides associated with them. Generally, this method works well for further defining particularly useful epitopes of tumor antigens.

In a typical method, either primary tumor cells or a cell line expressing the antigen of interest are provided. In addition, it will be recognized that phagocytic antigen presenting cells (or any APC), such as macrophages, may be fed large antigens (or portions thereof) and thus act as the starting material for these methods. The MHC class I or class II molecules can be isolated from these starting cells using known methods, such as antibody affinity (MHC-specific antibodies) and chromatographic techniques.

Isolated MHC molecules are then treated to release bound peptides. This may be accomplished by treatment with agents that disrupt the interactions between the bound peptide and the MHC molecule, for example, detergent, urea, guanidinium chloride, divalent cations, various salts and extremes in pH) The peptides released can be further purified using conventional chromatographic and antibody affinity (using antigen-specific antibody) methodologies. The purified peptides may then be subjected to sequence and structural determinations, using for example peptide sequencing, gas chromatography and/or mass spectroscopy.

In this manner the sequences/structures of the most prevalent peptide epitopes associated with class I and/or class II molecules may be determined. Supplied with this sequence/structural information, permutations of the determined sequence can be made, as detailed above, and assayed using known T-cell assays.

In an example presented below, this methodology was applied to the MUC-1 system. A 7-mer sequence (SEQ ID NO: 16), TSAPDTR, corresponding to part of the MUC-1 core repeat, was identified as a prevalent class I-associated peptide. Linear permutations of this peptide sequence were made which included: (SEQ ID NO: 17) GVTSAPDTR, (SEQ ID NO: 18) VTSAPDTRP, (SEQ ID NO: 8) TSAPDTRPA, (SEQ ID NO: 2) SAPDTRPAP, (SEQ ID NO: 19) APDTRPAPG, (SEQ ID NO: 20) PDTRPAPGS, and (SEQ ID NO: 21) DTRPAPGST. Each of these was assayed for a MUC-1-specific cytotoxic T-cell response and it was found that (SEQ ID NO: 8) TSAPDTRPA performed exceptionally well. Thus, this sequence represents a preferred antigen for generating MUC-1-specific activated T-cells according to the invention.

B. Liposome-encapsulated Antigen

In one embodiment of the invention, the antigen is encapsulated in a liposome. Techniques for preparation of liposomes and the encapsulation of various molecules, including peptides, in liposomes are well known to the skilled artisan. Liposomes are microscopic vesicles that consist of one or more lipid bilayers surrounding aqueous compartments. See, generally, Bakker-Woudenberg et al., (1993) *Eur. J. Clin. Microbiol. Infect. Dis.* 12 (Suppl. 1): S61, and Kim, (1993) *Drugs* 46: 618. Liposomes are similar in composition to cellular membranes and as a result, liposomes generally can be administered safely and are biodegradable.

Depending on the method of preparation, liposomes may be unilamellar or multilamellar, and can vary in size with diameters ranging from 0.02 $\mu$m to greater than 10 $\mu$m. A variety of agents can be encapsulated in liposomes. Hydrophobic agents partition in the bilayers and hydrophilic agents partition within the inner aqueous space(s). See, for example, Machy et al., LIPOSOMES IN CELL BIOLOGY AND PHARMACOLOGY (John Libbey 1987), and Ostro et al., (1989) *American J. Hosp. Pharm.* 46: 1576.

Liposomes can adsorb to virtually any type of cell and then release the encapsulated agent. Alternatively, the liposome fuses with the target cell, whereby the contents of the liposome empty into the target cell. Alternatively, an absorbed liposome may be endocytosed by cells that are phagocytic. Endocytosis is followed by intralysosomal degradation of liposomal lipids and release of the encapsulated agents. Scherphof et al., (1985) *Ann. N.Y. Acad. Sci.* 446: 368.

The following procedure may be used to prepare multilamellar (MLV-type), pH-insensitive, liposomes. The bulk liquid composition of the liposomes comprises: dipalmitoyl phosphatidyl choline (DPPC), cholesterol (Chol) and dimyristoyl phosphatidyl glycerol (DMPG) (Genzyme, Cambridge, Mass.) in a molar ratio of about 3:1:0.25 and at a final total lipid concentration of about 30 mM. Monophosphoryl lipid A (MPLA) (RIBI Immunochem Research Inc., Hamilton, Mont.) (or Avanti Lipid A; Avanti Polar Lipids, Inc.; 700 Industrial Park Drive, Alabaster, Ala. 35007) is included in the lipid mixture at a concentration of about 1% to about 5% (w/w) of bulk lipid, and the lipopeptide concentration is about 50 to about 1000 $\mu$g/mL. MPLA has been shown to serve as an effective adjuvant to cause increased presentation of liposomal antigen by the APCs to specific T Lymphocytes. Alving, C. R. 1993. *Immunobiol.* 187:430–446 (21).

The skilled artisan will recognize that other such adjuvants, such as Detox, alum, QS21, complete and/or incomplete Freund's adjuvant, MDP and LipidA, are also suitable. Bulk lipids, MPLA and lipopeptide (about 192 mg DPPC, about 33 mg Chol, about 15 mg DMPG, about 2.4 to 12 mg MPLA and about 0.6 to 12 mg of BLP-25 (25 aa from MUC-1) peptide for about 12 mL of final product) is dissolved in about 5.3 mL of ethanol. As used in this specification, a lipopeptide is a peptide that comprises an amino- or carboxy-terminal lipid moiety, such as palmitic acid, myristic acid, and the like.

In one embodiment, a lipopeptide such as BLP-25 (a palmitoylated MUC-1 peptide derivative) is used as the antigen peptide for encapsulation in liposomes. Thus, this lipopeptide derivative of MUC-1 is encapsulated in small, pH-insensitive liposomes along with MPLA.

The ethanol solution is warmed to about 50° C. and injected through a 30 g needle into about 100 mL of a suitable buffer, such as PBS, that is rapidly stirred at the same temperature. The resulting liposome suspension (largely small unilamellar vesicles, SUV) is depleted of ethanol and concentrated by diafiltration in a Sartorius cell with a molecular weight cutoff (MWCO) of about 300 kD. The volume is first reduced to about 10–20 mL, and then the product is washed by continuous replacement of the diafiltrate with about 100 mL of PBS. The volume is reduced to less than about 12 mL, and reconstituted to the final volume of about 12 mL after removal from the diafiltration cell.

Optionally, the product is then passed through a French pressure cell (SLM Aminco, Rochester, N.Y.), 3 times at 20,000 psi to ensure that all liposome particles are reduced to a size that would pass through a $0.22\mu$ filter that is used for sterilization. Size analysis shows that the mean particle size is slightly under $0.1\mu$.

Anionic liposomal vectors have also been examined. These include pH sensitive liposomes which disrupt or fuse with the endosomal membrane following endocytosis and endosome acidification.

Among liposome vectors, cationic liposomes are the most studied, due to their effectiveness in mediating mammalian cell transfection in vitro. They are often used for delivery of nucleic acids, but can be used for delivery of other therapeutics, be they drugs or hormones.

Cationic lipids are not found in nature and can be cytotoxic, as these complexes appear incompatible with the physiological environment in vivo which is rich in anionic molecules. Liposomes are preferentially phagocytosed into the reticuloendothelial system. However, the reticuloendothelial system can be circumvented by several methods including saturation with large doses of liposome particles, or selective macrophage inactivation by pharmacological means. Classen et al., (1984) *Biochim. Biophys. Acta* 802: 428. In addition, incorporation of glycolipid- or polyethylene glycol-derivatised phospholipids into liposome membranes has been shown to result in a significantly reduced uptake by the reticuloendothelial system. Allen et al., (1991) *Biochim. Biophys. Acta* 1068: 133; Allen et al., (1993) *Biochim. Biophys. Acta* 1150: 9.

Cationic liposome preparations can be made by conventional methodologies. See, for example, Felgner et al., *Proc. Nat'l Acad. Sci USA* 84:7413 (1987); Schreier, *J. of Liposome Res.* 2:145 (1992); Chang et al. (1988), supra. Commercial preparations, such as Lipofectin® (Life Technologies, Inc., Gaithersburg, Md. USA), also are available. The amount of liposomes and the amount of DNA can be optimized for each cell type based on a dose response curve. Felgner et al., supra. For some recent reviews on methods employed see Wassef et al., Immunomethods 4: 217–222 (1994) and Weiner, A. L., Immunomethods 4: 217–222 (1994).

Other suitable liposomes that are used in the methods of the invention include multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). The skilled artisan will recognize that the techniques for preparing these liposomes are well known in the art. See COLLOIDAL DRUG DELIVERY SYSTEMS, vol. 66 (J. Kreuter, ed., Marcel Dekker, Inc. 1994).

C. T-cells

Naive, memory, and anergic T-cells are prepared using techniques well known to the skilled artisan. For example, the following procedure is used. For T-cell enrichment, about $30-50\times10^6$ PBLs are suspended in 1 mL AIM-V media and loaded on 5 mL nylon wool columns (Robins Scientific, Sunnyvale, Calif.) that have been pre-conditioned with media. The loaded nylon wool columns are incubated at about 37° C. for about 45 minutes and then the non-adhering T-cells are eluted by washing with warm (about 37° C.) AIM-V media. The eluted T-cells are used as "naive" or anergic T-cells.

The skilled artisan will recognize that other well-known techniques may be used for preparing T-cells. A number of such techniques are described at pages 3.1.2 through 3.6.4 of CURRENT PROTOCOLS IN IMMUNOLOGY (John E. Coligan, ed., John Wiley & Sons, New York, 1991), hereby incorporated by reference. Commercially available columns are commonly used for T-cell enrichment, some of which are specific for enrichment of CD4+ and CD830 T-cells. Other methods include affinity beads such as Dyna beads (DYNAL, Lake Success, N.Y. 11042) and MiniMACS (Milteni Biotec. Inc., Auburn, Calif. 95603).

D. Antigen-presenting Cells

In one embodiment of the invention, peripheral blood lymphocytes (PBLs) are used as APCs. PBLs are isolated using art-recognized procedures. For example, the "buffy coat" is collected from peripheral blood samples using a method such as Ficoll-Hypaque gradient centrifugation is used to separate PBLs (peripheral blood lymphocytes) from other components. See the techniques described at pages 7.0.5 through 7.1.5 of CURRENT PROTOCOLS IN IMMUNOLOGY (John E. Coligan, ed., John Wiley & Sons, New York, 1991), hereby incorporated by reference E. Preparation of Activated T-Cells PBLs, naive or anergic T-cells, and liposome-encapsulated antigen are prepared as described above. Some of the PBLs are frozen and used as autologous APCs for later re-stimulations. All cell incubations are carried out in an incubator that has a temperature of about 37° C. and is supplied with $CO_2$ and humidity. In one embodiment, the T-cells used for activation and the PBLs used for APCs are autologous. Thus in one embodiment of the invention, the following procedure is used for preparing activated T-cells.

1) PBLs are combined with liposome-encapsulated antigen to make liposomal antigen-loaded PBLs. For example, about $10^4$ to about $10^9$ PBLs (e.g., ~2×$10^6$ PBLs) in 0.9 ml of AIM V (serum free lymphocyte medium) (Life Technologies) are added to a dose of liposome containing the lipopeptide formulation (e.g., about 0.1 μg to about 1 mg lipopeptide and about 0.1 μg to about 1 mg lipid such as MPLA in a volume of 0.1 ml in PBS) and are incubated for about 1 hour to about 18 hours at about 37° C. in a $CO_2$ supplemented incubator. Other suitable cell media are well-known in the art. Such media include, but are not limited to, RPMI 1640, DMEM and McCoys. Afterwards, the PBLs are treated with mitomycin C (or Gamma irradiation at 3000 rad) and then are washed.

2) (~1×$10^6$ T-cells and 1×$10^6$ liposomal antigen loaded PBLs)/ml (from step (1)) are suspended in a total of about ~10 ml AIM V media in a 25 $cm^2$ tissue culture vessel (such as a flask or plate) and put in a 37° C. incubator. T-cells and PBLs can be used in a range of about $10^3$ to about $10^7$ cells per well.

3) After about 24 h, recombinant IL-7 (10 ng/ml) (Intermedico, Markham, Ontario) and IL-12 (100 pg/ml)(R & D Systems, Minneapolis, Minn.) are added to the mixture of step (2) and incubated for 5–7 days at 37° C. with $CO_2$. IL-12 has been shown to favor a shift towards TH1 pattern in the cytokine profile of developing CD4+ T-cells. Hsieh, et al. 1993. *Science*. 260:547–549 (27). The skilled artisan will recognize that TH1 response patterns are characterized by the production of IL-2 and gamma-IFN, in a relative absence of IL-4, IL-6 and IL-10. IL-12 also synergistically acts in the induction of γ-IFN production during primary activation of CD8+ T-cells. Gajewski, et al. 1995. *J. Immunol.* 154:5637–5648. Recombinant IL-7 (rIL-7) has been previously demonstrated to enhance the growth and differentiation of precursor CTL. Alderson, et al. 1990. *J. Exp. Med.* 172:577–587; Kos, et al. 1992. *Eur. J.* Immunol. 22:3183–3185.

Other suitable cytokines are also used in this step. For example, IL-1, IL-2, IL-4, gamma interferon or IL-15 are used in any combination. Suitable combinations include, but are not limited to, IL-2 and IL-4; IL-2 and IL-5; IL-2 and gamma-IFN; IL-2 and IL-1. The skilled artisan will recognize that the concentrations and combinations of the cytokines used for activation will vary according to the cells, experimental conditions and cytokines chosen. Optimal levels may be determined by assaying for optimal T-cell stimulation.

4) Following step (3), all T-cells and PBLs are collected and fresh APCs are added and the mixture is incubated for about 24 hours. The APCs added at this step are loaded with liposomes that have been loaded with peptide antigen, as described in step (1).

5) After step (4) additional IL-7 (about 1 to about 50 pg/ml) and IL-12 (about 10 to about 500 pg/ml) are added to the culture medium. In one embodiment, 10 ng/ml of IL-7 and 100 pg/ml of IL-12 is used.

6) The cell mixture is incubated for about 5–7 days in the incubator at 37° C. with $CO_2$ and humidity. At this point, supernatant is collected for cytokine screening. Such material is kept at −80° C. until used for screening.

7) The resultant activated T-cells are collected using procedures well known to the skilled artisan. In a typical procedure, cells and media present in the tissue culture flask are isolated and cells are washed twice with AMV medium, and are used as harvested cells. Alternatively, live cells are separated by using a FICOLL procedure similar to that for isolating PBLs.

F. Characterization of T-cells

1. Proliferation Assays

T-cell proliferation assays are well known in the art. Such assays are used to determine whether a specific antigen stimulates T-cell proliferation. For example, such an assay is set up using 96 well plates using about $10^5$ T-cells and 5×$10^4$ APCs/well/200 μl in AIM V medium. Other T-cell and APC concentrations may be used. APCs are pre-treated with mitomycin C to inhibit proliferation. APCs loaded with control or experimental soluble peptides, and liposomes containing peptide or lipopeptide are used as agents for stimulation of T-cells. After about 5–6 days, the cells are pulsed with $^3$H-Tdr (about 1 μCi/well). 12–18 hours after pulsing, the cells are harvested and $^3$H-Tdr incorporation into T-cells is measured.

A suitable cell harvester collects the cells on filter paper. Uptake of radioactivity into T-cells is assessed by measuring radioactivity bound on, or trapped on, the filter paper.

2. Assessment of CD Antigens on T-cell Surface

Art-recognized techniques are used to determine which CD antigens are present on the surface of activated T-cells. Typically, anti-CD antigen antibodies that are labeled with fluorochromes are used to "stain" the T-cells which is assessed via fluorescence microscopy or via a fluorescence activated cell sorter (FACS) used in the cytometry mode. See Volume 1, Chapter 5 (Immunofluorescence and Cell Sorting) In CURRENT PROTOCOLS IN IMMUNOLOGY (John E. Coligan, ed., John Wiley & Sons, New York, 1995), hereby incorporated by reference.

3. Cytokine Production

Measurement of cytokine production by cells is carried out using art-recognized techniques. The skilled artisan will know that the concentration of a cytokine, such as an interleukin, or an interferon, in cell culture medium is measured using ELISA techniques. Cytokines such as interleukins are detected by bioassays, in which a given cytokine leads to the stimulation of a specific cell type. Suitable cytokine detection techniques are an ELISPOT assay, and intracellular cytokine determination using flow cytometry. See Volume 1, Chapter 2 in CURRENT PROTOCOLS IN IMMUNOLOGY (John E. Coligan, ed., John Wiley & Sons, New York, 1991), hereby incorporated by reference.

G. Research Techniques

In one embodiment of the invention, the invention relates to a method for identifying antigens and epitopes that are effective in generating an antigen-specific T-cell response. This method comprises the following steps:

(1) Prime suitable cultured cells (T-cells, PBLs) with various peptides that are antigen and epitope candidates; and (2) Assess proliferation and cytokine production of the cells primed in step (1).

Proliferation and cytokine production are assessed as described above. Alternatively, cytokine production is assessed using the following method. A sandwich-type ELISA assay is used in which one antibody against the analyte (cytokine to be analyzed) is attached to the solid phase (such as a 96 well plate) and is thus used to bind (or capture) the cytokine. A sample to be analyzed for analyte is exposed to the solid phase. After binding and washing, a second anti-analyte antibody (which comprises a reporter group) is added. Suitable reporter groups include, but are not limited to, radioactive isotopes, fluorescent groups, and enzymes (horse radish peroxidase (HRP), alkaline phosphatase, β-galactosidase). Reporter-labeled antibodies are incubated for a suitable time and the solid phase is washed to remove unbound reporter. Appropriate detection technology is then employed to determine the amount of analyte in the sample (e.g., radioactivity measurement; chromogenic or colorimetric assessment (for enzyme-conjugated antibody)) by comparison of sample values with known standards.

The skilled artisan will recognize that well-known techniques can be used for deletion and mutation of specific amino acids in a given antigen. Using such techniques, the epitopes required for the desired T-cell activation are identified. For example, an overlapping sequence mapping technique is used. Typically, nine amino acid-long peptides from a candidate antigen are tested for T-cell stimulating activity. A series of peptides is made by making overlapping nine-aa sequences by progressing through a known protein sequence, one amino acid at a time. In this way, the peptide with the highest T-cell stimulating activity is identified.

In another embodiment, the invention relates to a method for characterizing the T-cell immune response, comprising:
 (1) generating a T-cell response against an antigen of interest; and
 (2) characterizing the T-cell response by assessment of cell surface antigen identity, cytokine production, and other parameters that are well known to the skilled artisan. For example, type 1, type 2, type 3, and type 0 are known T-cell response types.

H. Therapeutic Methods

Using a method according to the invention, various peptides are used to generate cellular vaccines for immunotherapy. Such vaccines are, for example, peptide antigen-loaded APCs, such as autologous PBLs. In addition, antigen-stimulated T-cells can also be used for vaccination, a technique known as "adoptive T-cell transfer therapy." Vaccines according to the present invention are used for (a) prevention of disease development following vaccine administration to a patient and/or (b) treatment of a patient with a disease.

For example, the BLP-25 peptide antigen is incorporated into a liposome and used to load PBLs (from a patient) with antigen, as described above. The loaded PBLs can be injected back into patients as cellular vaccines. The loaded PBLs also can be used to activate autologous T-cells in vitro, as described above. This creates an expanded population of antigen-specific T-cells. These activated T-cells are then re-administered to a patient suffering from, for example, an adenocarcinoma. For a description of art-recognized techniques for adoptive T-cell transfer therapy, see Bartels, et al. *Annals of Surgical Oncology,* 3(1):67 (1996), hereby incorporated by reference.

A T-cell activation method according to the invention is also used to generate cytotoxic and helper T-cell responses to antigens that are candidates for use as vaccines, in immunotherapy, or for various pathological conditions, such as cancer, tumors, viral infections, and bacterial infections. Thus, using a method according to the invention, a candidate antigen is selected, encapsulated in a liposome, used to load autologous PBLs, and the loaded PBLs are injected into the patients, or alternatively the PBLs are used to activate autologous T-cells. The stimulated T-cells are re-administered to a patient suffering from one of the aforementioned disorders. The skilled artisan will recognize that peptide antigens are selected based on the type of disease affecting the patient. For example, MUC-1 antigens are used for making antigen-specific T-cells that are used in therapy of adenocarcinoma. Other examples include, but are not limited to, the following antigens.

In one embodiment, the epitope is a parasite-associated epitope, such as an epitope associated with leishmania, malaria, trypanosomiasis, babesiosis, or schistosomiasis. Suitable parasite-associated epitopes include, but are not limited to, the following.

| Parasite | Epitope | References |
| --- | --- | --- |
| Plasmodium Falciparum (Malaria) | (NANP)3 (SEQ ID NO: 34) Circumsporoz. protein AA 326–343 | Good et al. (1986) J. Exp. Med. 164:655 Good et al. (1987) Science 235:1059 |
| Leishmania donovani | Repetitive peptide | Liew et al. (1990) J. Exp. Med. 172:1359 |
| Leishmani major | EAEEAARLQA (SEQ ID NO: 22) (code) | This application |
| Toxoplasma gondii | P30 surface protein | Darcy et al. (1992) J. Immunolog. 149:3636 |
| Schistosoma mansoni | Sm-28GST antigen | Wolowxzuk et al. (1991) J. Immunol 146:1987 |

In another embodiment, the epitope is a viral epitope, such as an epitope associated with human immunodeficiency virus (HIV), Epstein-Barr virus (EBV), or hepatitis. Suitable viral epitopes include, but are not limited to:

| Virus | Epitope | Reference |
| --- | --- | --- |
| HIV gp120 | V3 loop, 308–331 | Jatsushita, S. et al. (1988) J. Viro. 62:2107 |
| HIV GP120 | AA 428–443 | Ratner et al. (1985) Nature 313:277 |
| HIV gp120 | AA 112–124 | Berzofsky et al. (1988) Nature 334:706 |
| HIV | Reverse transcriptase | Hosmalin et al. (1990) PNAS USA 87:2344 |
| Flu | nucleoprotein AA 335–349, 366–379 | Townsend et al. (1986) Cell 44:959 |
| Flu | haemagglutinin AA48–66 | Mills et al. (1986) J. Exp. Med. 163:1477 |
| Flu | AA111–120 | Hackett et al. (1983) J. Exp. Med 158:294 |
| Flu | AA114–131 | Lamb, J. and Green N. (1983) Immunology 50:659 |
| Epstein-Barr | LMP43–53 | Thorley-Lawson et al. (1987) PNAS USA 84:5384 |
| Hepatitis B | Surface Ag AA95–109; AA 140–154 Pre-S antigen AA 120–132 | Milich et al. (1985) J. Immunol. 134:4203 Milich, et al. (1986) J. Exp. Med. 164:532 |
| Herpes simplex | gD protein AA5–23 | Jayaraman et al. (1993) J. Immunol. 151:5777 |
| | gD protein AA241–260 | Wyckoff et al. (1988) Immunobiology 177:134 |
| Rabies | glycoprotein AA32–44 | MacFarlan et al. (1984) J. Immunol. 133:2748 |

The epitope may also be associated with a bacterial antigen. Suitable epitopes include, but are not limited to:

| Bacteria | Epitope ID | Reference |
| --- | --- | --- |
| Tuberculosis | 65Kd protein AA112–126 AA163–184 AA227–243 AA242–266 AA437–459 | Lamb et al. (1987) EMBO J. 6:1245 |
| Staphylococcus | nuclease protein AA61–80 | Finnegan et al. (1986) J. Exp. Med. 164:897 |

-continued

| Bacteria | Epitope ID | Reference |
|---|---|---|
| E. coli | heat stable enterotoxin | Cardenas et al. (1993) Infect. Immunity 61:4629 |
| | heat liable enterotoxin | Clements et al. (1986) Infect. Immunity 53:685 |
| Shigella sonnei | form I antigen | Formal et al. (1981) Infect. Immunity 34:746 |

Thus, an efficient T-cell response is generated in humans against tumor associated self antigenic peptides (cryptic self) in vitro. As noted above, MUC-1 peptides are used to treat adenocarcinoma.

It has been observed that the T-cells of patients with certain types of cancer and viral infections become unresponsive, or anergic, to stimulation with peptide antigens. In a number of studies, this lack of T-cell responsiveness has been attributed to detects in IL-2 production following stimulation with peptide antigen. Upon the addition of exogenous IL-2, the T-cells become responsive to antigen. See Beverly, et al. *International Immunology* 4(6):661 (1992), and Wotton, et al. *Human Immunology* 42(2):95 (1995). However, the administration of high levels of IL-2 in vivo has toxic side effects. These side effects are significantly reduced when the IL-2 is encapsulated in a liposome prior to administration.

Accordingly, in another embodiment, the invention includes a method for boosting T-cell immune response and reversing T-cell anergy in vitro against peptide antigens. A typical method comprises co-culturing anergic or naive T-cells with free IL-2 or oncolipin (IL-2 encapsulated in a liposome), followed by activation of the resultant T-cells with antigen-loaded APCs.

The foregoing detailed description and the following examples illustrate the invention, but do not limit the scope of the invention.

EXAMPLES

Example 1

This example illustrates the use of the MUC-1 model to generate a class I-restricted antigen-specific cytotoxic T-cell response.

1. Materials and Methods

Peptides. Various synthetic peptides were prepared by automated solid phase synthesis with Fmoc amino acids using a Milligen/Bioresearch Model 9050 Peptide Synthesizer (Millipore, Marlborough, Mass.). The following peptides were used for these studies which were 95% pure, as determined by HPLC: a human MUC-1 24-amino acid peptide (BP24) (SEQ ID NO: 23), previously referred to as p-24H (Agrawal et al., Cancer Research (1995) (amino acid sequence for BP24: TAPPAHGVTSAPDTRPAPGSTAPP); BP-25 (SEQ ID NO: 5) (amino acid sequence for BP-25: STAPPAHGVTSAPDTRPAPGSTAPP), a mouse MUC-1, 24-amino acid peptide (BP-24M) (SEQ ID NO: 24) DSTSSPVHSGTSSPATSAPEDSTS; any of the preceding peptides containing a palmitoyl group at a lysine residue added to the carboxy terminal end of the peptide (lipopeptides). BLP-24 and BLP-25, for instance, are lipopeptide versions of BP-24 and BP-25, respectively, having a palmitoyl group at the epsilon amino group of an added lysine near the carboxy terminus. BLP-25 has the amino acid sequence of BP-25 plus additional lysine and glycine residues and BLP-24 is the same analog of BP-24.

Antibodies. W6/32 (pan anti-HLA class I antibody). OKT8 (anti-CD8) and OKT4 (anti-CD4) antibodies were used to block T-cell responses. The antibodies (W6/32, OKT4, OKT8) and their isotype control antibodies were purified from culture supernatants of hybridomas obtained from ATCC. For FACs staining anti-CD4-FITC/anti-CD8-PE, anti CD25-PE and anti CD3-PE, anti CD28-PE, anti TCRαβ-FITC, CD4-FITC, CD8-FITC, CD3-FITC, CD69-PE and isotype control antibodies were obtained from Becton and Dickinson (Mountain View, Calif.).

Preparation of Liposomes—Ethanol Injection Process. The bulk liquid composition of liposomes consisted of dipalmitoyl phosphatidyl choline (DPPC), cholesterol (Chol) and dimyristoyl phosphatidyl glycerol (DMPG) (Genzyme, Cambridge, Mass.) in a molar ratio of 3:1:0.25 and at a final total lipid concentration of 30 mM. Monophosphoryl lipid A (MPLA) (RIBI Immunochem Research Inc., Hamilton, Mont.) was included in the lipid mixture at a concentration of 1 to 5% (w/w) of bulk lipid, and the lipopeptide concentration was 50 to 1000 $\mu$g/mL. Bulk lipids, MPLA and lipopeptide (192 mg DPPC, 33 mg Chol, 15 mg DMPG, 2.4 to 12 mg MPLA and 0.6 to 12 mg of lipopeptide) for 12 mL of final product were dissolved in 5.3 mL of ethanol. The ethanol solution was warmed to 50° C. and injected through a 30 g needle into 100 mL of PBS that was rapidly stirred at the same temperature. The resulting liposome suspension (largely small unilamellar vesicles, SUV) was depleted of ethanol and concentrated by diafiltration in a Sartorius cell with a molecular weight cut-off (MWCO) of 300 kD. The volume was first reduced to 10–20 mL, and then the product was washed by continuous replacement of the diafiltrate with 100 mL of PBS. The volume was reduced to less than 12 mL, and reconstituted to the final volume of 12 mL after removal from the diafiltration cell. The product was then passed through a French pressure cell (SLM Aminco, Rochester, N.Y.), 3 times at 20,000 psi to ensure that all liposome particles would be reduced to a size that would pass through a $0.22\mu$ filter that was used for sterilization. Size analysis showed that the mean particle size was slightly under $0.1\mu$.

Cytokines. Human recombinant cytokines, IL-12 (R&D Systems, Minneapolis, Minn.), MN), IL-7 (Intermedico, Markham, Ontario) were diluted in serum-free AIM-V media (Life Technologies) just prior to use.

General Procedures for Loading APCs with Liposome-encapsulated peptide. Human peripheral blood lymphocytes (PBLs) were purified from heparinized blood by centrifugation in Ficoll-Hypaque (Pharmacia, Uppsala, Sweden). The Ficoll-blood interface layer obtained by centrifugation was collected and washed twice with RPMI before use.

Briefly, to $2\times10-10^6$ PBLs in 0.9 mL AIM-V media, one dose of liposome containing lipopeptide formulation was added and the PBLs were incubated overnight at 37° C. with $CO_2$ supplemented incubator. After incubation, the PBLs were treated with mitomycin C or γ-irradiated (3000 rads) followed by washing with AIM-V media.

T-cell Culture in Bulk For T-cell enrichment, $30–50\times10^6$ PBLs were suspended in 1 mL AIM-V media and loaded on media pre-conditioned 5 mL nylon wool columns (Robins Scientific, Sunnyvale, Calif.). The loaded nylon wool columns were incubated at 37° C. for 45 minutes and then the non-adhering T-cells were eluted by washing with warm (37° C.) AIM-V media. Initially, the bulk culture was started in a 25 cm² tissue culture sterile flask (Corning Glass, Corning, N.Y.). $10^7$ T-cells were cultured in the presence of $10^7$ antigen loaded, gamma-irradiated autologous PBLs in a total volume of 10 mL in AIM-V media for 16–24 hours, at which time the culture was fed with human rIL-7 (10 μg/mL) and human rIL-12 (100 pg/ml), and left for 6–8 more days. At the end of the 7–10 days of culture, surviving t-cells were collected and re-stimulated with autologous APCs loaded with liposomal antigen. After two consecutive cycles of re-stimulation (14–16 days), the T-cells were collected, and counted. The supernatant was collected from bulk cultures at 14 days for cytokine screening and kept frozen at −80° C. until used for the assay. Repeated freeze/thaw was prevented.

T-Cell Proliferation Assay T-cells ($5\times10^4$–$1\times10^5$) obtained at the end of 14–16 days of culture, as described above, were incubated in the presence of various antigen-containing liposomes, soluble BP24, soluble BLP-24M, loaded or unloaded autologous liposomes, and mitomycin C treated APCs ($5\times10^4$–$10^5$), in a total volume of 200 μL in AIM-V medium, in 96-well flat-bottom tissue culture plates—for a period of 5 days at 37° C., 7% $CO_2$ and moisture. Each group was cultured in 5 replicate wells. At the end of 5 days, 100 μL of culture supernatant was collected from each well and tested for the presence of γ-IFN or IL-4 by ELISA, as described below. After collecting the supernatant for cytokines, 1 μCi $^3$H-Tdr (Amersham Canada Limited, Oaksville, Ontario) was added into each well and incubated overnight. Incorporation of $^3$H-Tdr into DNA of proliferating cells was measured after harvesting the plates and counting in the matrix beta counter.

Cytotoxic T lymphocyte assays. For the CTL assay, three (HLA.A2$^+$) normal donors' PBLs were used. The T-cells were grown for two weeks in bulk cultures as described above. At the end of two weeks, live T-cells were harvested from flasks and counted. The targets were mutant T2 cells. Houbiers et al., Eur. J. Immunol 23:2072–2077 (1993); Stauss et al., Proc. Natl. Acad. Sci. U.S.A. 89:7871–7875 (1992). The MUC-1 peptide-mediated upregulation of HLA.A2 expression on T2 cells was examined using the MUC-1 nine-mer peptides (SEQ ID NO: 25) ATAPPAHGV and SAPDTRPAP using known methods. Townsend et al., Nature 346:476 (1989). T2 cells were loaded overnight with various MUC-1 synthetic peptides at 200 μM in presence of exogenous β2m. Houbiers et al., Eur. J. Immunol 23:2072–2077 (1993); Stauss et al, Proc. Natl. Acad. Sci. U.S.A. 89:7871–7875 (1992). These peptide-loaded T2 target cells were then loaded with $^{51}$Cr (using NaCrO$_4$) for 90 min and washed extensively. CTL assays were performed as previously described. Agrawal et al., J. Immunol. 156:2089 (1996). Percent specific killing was calculated as: experimental release—spontaneous release/maximum release—spontaneous release×100. The effector versus target ratios used were 10:1, 20:1, 60:1, and 120:1. Each group was set up in four replicate and mean percent specific killing was calculated.

Estimation by ELISA of γ-IFN, IL-10 and IL-4 Produced in Culture Supernatant The supernatant fractions collected from the bulk cultures were examined separately for γ-IFN and IL4 and IL-10. In the proliferation assay plate, the supernatants were collected individually and then tested for the presence of γ-IFN and IL4.

For the γ-IFN assay, 96-well Nunc ELISA plates were coated overnight at 4° C. with mouse anti-human γ-IFN monoclonal antibody (Genzyme, Cambridge, Mass.) in NaHCO$_3$ buffer (0.1 M, pH 9.5). Test sample as well as positive control human γ-IFN (R&D Systems) and recombinant γ-IFN reference standards were then incubated for 2 hours followed by a second antibody (goat anti-human γ-IFN) for two hours, followed by incubation with the third antibody (Biotin donkey anti-goat IgG) for 45 minutes at room temperature. This incubation step was followed by incubation with conjugate (peroxidase conjugated streptavidin, Jackson Laboratories, Bar Harbour, Me.) for 30 minutes and the addition of ABTS peroxidase substrate and $H_2O_2$ (Kirkegaard and Perry Laboratories, Gaithersburg, Md.). At this time, the plates were read in the ELISA reader (Molecular Devices Corporation, Menlo Park, Calif.) in kinetic mode [Molecular Thermomax dual wavelength (405–490 nm)].

For the IL-4 assay, the ELISA was a two-step procedure and the peroxidase conjugated streptavidin step came after incubation with the second antibody (Biotin mouse anti-human IL-4). Most of the reagents and monoclonal antibodies were obtained from Pharmingen (San Diego, Calif.). The range of quantification of cytokine detected was 31–1000 pg/mL for IL-4 and 25–800 pg/ML for γ-IFN.

For the IL-10 assay, the ELISA was a two step procedure where the in incubation with second antibody (Biotin rat anti-human and viral IL-10 polyclonal antibody) was followed with incubation with peroxide-conjugated streptavidin. All of the monoclonal and polyclonal antibodies were purchased from Pharmingen (San Diego, Calif.). The range of IL-10 detection was 100–6400 pg/mL.

Cell Surface Immunofluorescence Staining. For detection of cell surface antigens, the T-cells harvested from bulk culture (as described previously) were washed once in cold PBS containing 1% BSA followed by addition of 10 μl goat Ig (3 mg/ml) to the cell pellet and incubated for 10 min on ice, to which was added 50 μl of PBS containing 1% BSA and 3% human AB serum.

For indirect staining, the cells were incubated with test antibody or isotype control antibody (2 μg $5\times10^5$ T-cells) for 30–45 min on ice. 100 μl of PBS containing 10% BSA was added and cells were washed once in cold PBS at 4° C. The second antibody, Goat anti mouse IgG1-PE (70 μl of 1:100 dilution) diluted in PBS containing 1% BSA and 3% human AB serum, was added and incubated for 30–45 min on ice at 4° C. PBS containing 10% BSA (200 μl) was added and cells were washed once in PBS at 4° C. For directly labeled test antibody, only single incubation step was performed. For single staining, cells were resuspended in 2% paraformaldehyde (PFA) containing PBS. For double staining, 10 μl of mouse Ig (3 mg/ml) were added to the cell pellet and left on ice for 10 min and added with 50 μl of PBS containing 1% BSA and 3% human AB serum. 10 μl of second directly labeled antibody were added and incubated for 30–45 min on ice, followed by addition of 10 μl of 10% BSA containing PBS, washing once in cold PBS and re-suspending in 2% PFA containing PBS. In parallel, appropriate isotype control antibody was always used to stain the cells in a similar way. The samples were generally run and analyzed by flow cytometry using FACSort$^R$ (Becton & Dickinson). Percent positive cells were defined as the fraction of cells exhibiting fluorescence intensities beyond a region set to exclude at least 98% of the control isotype matched antibody stained cells.

2. Results

A. Induction of in vitro T-cell Response Against Synthetic MUC-1 Lipopeptide

The synthetic MUC-1 lipopeptide (BLP-25) used in these studies was chosen due to the fact that it has the capacity to bind to several HLA class I molecules e.g. HLA-A11, A3, A2.1 & A1. Domenech et al., (1995) *J. Immunol.* 155:4766. In addition, it has been shown that MUC-1 peptide BP-24 (which is contained within the sequence of BLP-25) is a permissive epitope for HLA class II restricted CD4$^+$ T-cell response. Agrawal et al., *Cancer Res.* 55, *supra*. BLP-25 is the amino acid sequence BP-25, with a palmitoyl chain attached to the carboxy-terminal end of the peptide. The lipid side chain facilitates binding of the BP-25 peptide to a liposome.

BP-24 lacks the amino terminal serine of BLP-25 (and BP-25). It was shown previously that the amino terminal serine present in BLP-25 (and BP-25) gives it additional ability to bind to several HLA class I molecules. Domenech et al., supra.

The primary, secondary and tertiary in vitro T-cell proliferative response of PBLs isolated from buffy coats of normal red cross donors (n=4) against BLP-25 in soluble form was measured, using the method described in Agrawal et al., (1995) Cancer Res. 55:2257. In all $1°$, $2°$ and $3°$ stimulations, no significant antigen specific T-cell proliferation (S.I.<3) was observed.

Using the ethanol-injection procedure described above, suv containing BLP-25 lipopeptide and monophosphoryl lipid A (MPLA) were prepared. Naive T-cells were isolated from PBLs of normal red cross donors as described above and cultured in presence of autologous PBLs loaded with BLP-25 or control antigen-containing SUV liposomes. T-cells were cultured with autologous, mitomycin C treated-PBLs that had been pre-loaded with a BLP-25 liposome preparation containing various concentrations of the peptide. Culturing was carried out for 1 wk, 2 wk or 3 wk, with weekly restimulation with autologous APCs (BLP-25 antigen/liposome-loaded).

When soluble peptide antigen was used to stimulate naive T-cells, no peptide specific proliferative response was observed during the $1°$ and $2°$ stimulations. However, when the T-cells were stimulated twice with antigen-liposome loaded autologous PBLs in a two week time period, and then tested for the proliferative response against a number of test or control antigen-peptide liposome loaded autologous APCs, there was a strong antigen-specific T-cell proliferative response, as measured by $^3$H-thymidine incorporation. The proliferative response of T-cells was dependent on the dose of antigen peptide BLP-25 in the liposome preparations. Thus, a strong proliferative response was observed in naive T-cells treated with a liposome-encapsulated MUC-1 peptide.

The following controls were used. The response of T-cells cultured with APCs loaded with BLP-25 liposome was compared with (1) soluble antigen peptides: BP24, BP24M and (2) liposomes containing a mouse homolog of BLP-25, the BLP-24M lipopeptide. There was no proliferative T-cell response against these control antigen peptides. The proliferative responses of the T-cells from donor PBLs against BLP-25/liposomes were categorized into three groups. Out of 17 donors, 6 were "high responders" to BLP-25 (FIG. 1A); 7 donors were "medium responders" (FIG. 1B) and T-cells from 4 donors did not show any T-cell proliferative response against BLP-25 (FIG. 1C). The difference in T-cell responsiveness may be attributed to different MHC haplotypes of the individual donors.

Upon stimulation of T-cells from high responder donors with soluble BLP-25 peptide, no peptide-specific proliferation was observed.

Another experiment was conducted to study the response of T-cells cultured in the presence of (1) autologous PBLs loaded with BLP-25 liposomes; (2) autologous PBLs loaded with BLP-24 liposomes; and (3) BLP-24M liposomes (FIG. 3A and 3B). It was observed that there was a proliferative response against BLP-24 liposomes but not against BLP-24M liposome. The response to BLP-24 was not as strong as the response to BLP-25. This may be due to additional epitopes provided by the amino-terminal serine residue on BLP-25. It is known that this serine residue confers additional HLA-binding capability on BLP-25. Domenech et al., supra.

B. MUC-1 Peptide BLP-25 Responsive T-cells Produce Type-1 Cytokines in the Supernatant in an Antigen Dependent Manner Culture supernatants were collected from the media of bulk cultured T-cells that had been stimulated with BLP-25 liposome-loaded autologous PBLs, at the end of 2 stimulations (i.e. after 2 weeks of culturing). The supernatant was tested for the presence of secreted cytokines γ-IFN, IL-4, and IL-10 by ELISA assays, as described above. There was a significant concentration of γ-IFN and some IL-10 (Table 1). Only undetectable or small quantities of IL-4 were detected in the culture supernatant. The amount of γ-IFN correlated with the dose and specificity of the antigen peptides.

TABLE I

Cytokines produced in the supernatant of bulk cultures of T-cells cultured in presence of autologous APCs loaded with MUC-1 lipopeptide containing liposomes

| Stimulatory antigens | IFN-γ (pg/ml) ± S.D. | IL-4 (pg/ml) ± S.D. | IL-10 (pg/ml) ± S.D. |
| --- | --- | --- | --- |
| No lipopeptide | 105.10 ± 57 | 36.02 ± 45 | <100.00 |
| BLP 25, 1 ug | 63.55 ± 45 | 37.06 ± 6 | <100.00 |
| BLP 25, 10 ug | 452.40 ± 6.00 | <31.00 | 289.50 ± 3.00 |
| BLP 25, 100 ug | 1244.00 ± 359.00 | 74.09 ± 3.00 | 206.9 ± 17.00 |
| BLP 24, 10 ug | 517.0 ± 30.00 | <31.00 | 199.10 ± 10.00 |
| BLP 24, 100 ug | 722.50 ± 119.00 | <31.00 | 217.90 ± 0.0 |

The data shown in this table are representative of >3 repeated experiments (with 3 different high responder donors). The ranges of sensitivity of cytokine ELISA assays were 25–1600 pg/ml (for IFN-γ), 31–2000 pg/ml (for IL4) and 100–6400 pg/ml (for IL-10). The supernatant was collected at approximately two weeks of in vitro culture in presence of the stated antigens loaded autologous APCs.

There was significantly less γ-IFN (~100–200 pg/ml) produced in the supernatant from culture of no responder T-cell groups. The supernatant from the T-cells cultured in the presence of autologous PBLs loaded with empty liposomes (with MPLA, but no peptide) had a very low level of γ-IFN (~100 pg/ml) in contrast to the supernatant from cells cultured with PBLs loaded with peptide containing liposomes (γ-IFN levels of about 450 to about 1200 pg/ml).

Table II shows the cytokines secreted in the supernatants in 96 well microtiter plate during proliferation assays. The quantity of γ-IFN produced was in agreement with dose and specificity of peptide specific T-cell proliferative response. However, there was low level production of γ-IFN (~200 pg/ml) in T-cells stimulated with liposomes without peptide or soluble peptide controls, probably due to presence of MPLA in the liposomal preparation used to stimulate these T-cell cultures. Overall, the amount of IL-4 produced in the supernatant was much lower compared to γ-IFN and was in the range of <100 pg/ml (Table II).

TABLE II

Cytokines secreted in the supernatant in the microtiter wells of 96 well plate in the proliferation assay of T cells stimulated with autologous PBLs loaded with liposomes containing BLP-25, 100 ug dose.

| Stimulatory antigens | IFN-γ (pg/ml) ± S.D. | IL-4 (pg/ml) ± S.D. |
| --- | --- | --- |
| Liposomal formulation | | |
| No lipopeptide | 244 ± 2 | <31.00 |
| BLP 25, 1 ug | 399 ± 8 | <31.00 |
| BLP 25, 10 ug | 496 ± 59 | <31.00 |
| BLP 25, 100 ug | 983 ± 140 | <31.00 |
| BLP 24, 10 ug | 466 ± 9 | <31.00 |
| BLP 24, 100 ug | 492 ± 10 | <31.00 |
| Soluble peptides[a] | | |
| BP-24 peptide (100 ug) | 131 ± 0 | 35 ± 15 |
| BLP-25 peptide (100 ug) | 152 ± 7 | 61 ± 22 |
| BP-24M (100 ug) | 193 ± 79 | <31.00 |

The data shown in this table are representative of >3 repeated experiments (with 3 different high responder donors). The range of sensitivity of cytokine ELISA assays were 25–1600 pg/ml (for IFN-γ), 31–2000 pg/ml (for IL4). The supernatant was collected on the 6th day of proliferation assay from individual wells of 4–5 replicate wells and the results are shown as avg. S.D. a T-cells grown with liposomal antigen loaded APCs for two weeks were cultured in presence of autologous APCs loaded with soluble peptides in 96 well plates on the 6th day of the culture, the supernatant was collected and tested for presence of secreted cytokines.

C. Blocking the BLP-25 Peptide Specific T-cell Proliferative Response by Monoclonal Antibodies Against CD4 and CD8

Monoclonal antibodies (Mabs) against (1) CD4; (2) CD8; and (3) HLA class I molecules, and their respective isotype control antibodies, were used in proliferation assays to examine the types of T-cells responding to the BLP-25 peptide in in vitro cultures. As shown in FIG. 4, both anti CD4 and anti CD8 mAbs partially blocked the antigen specific T-cell proliferative responses. Anti HLA class I (W6/32) also partially blocked the T-cell proliferative response. As controls, the respective isotype control antibodies did not block the T-cell proliferative response. These results indicated that both $CD4^+$ and $CD8^+$ T-cell responses were generated.

D. Phenotype of T-cells Responding to BLP-25 Peptide Presented as Liposomal-treated Autologous PBLs as APCs Flow cytometry experiments were performed to examine the phenotype of T-cells in the responder cultures (FIGS. 5A and 5B). The presence of activation markers CD25 and CD69 were examined in context of $CD4^+$ or $CD8^+$ T-cells. The skilled artisan will recognize that CD3 and αβTCR are markers for T-cells. CD28 is a ligand for B7.1 and B7.2. CD69 is an "early" T-cell activation antigen. CD25 (IL-2 receptor) is also a T-cell activation antigen, which has high affinity for IL-2.

The presence of CD3, αβTCR, and CD28 on the surface of in vitro cultured T-cells suggests that normal T-cells, which are also antigen-specific, are generated in the present studies using in vitro techniques. This also indicates that the present methodology does not produce non-physiological artifacts. The presence of high-density CD25 (IL-2 receptor) on cultured T-cells, that was determined using flow cytometry, suggests that these cells are activated and respond to IL-2.

In addition, the T-cells from BLP-25 responder cultures were examined for the presence of αβ TCR and expression of CD28 molecules (FIGS. 5A and 5B). Most of the $CD3^+$ T-cells were TCRαβ+ and $CD28^+$. The CD4/CD8 ratio in these in vitro cultures was approximately 2:1 (FIG. 5A). Among the $CD4^+$ cell population, approximately 50% of the cells were $CD25^+$ and 25% cells were $CD69^+$ (FIG. 5B). Among the $CD8^+$ T-cell population, approximately 30–40% of the cells were $CD25^+$ and approximately 50–60% cells were $CD69^+$. All of the $CD4^+$ and $CD8^+$ cell population were $TCRαβ^+$ and $CD28^+$.

It was also determined that the percentage of activated T-cells with CD25 and CD69 expression at a given time in culture is higher in cultures which have been stimulated with autologous APCs loaded with liposomal antigen peptide, when compared to cultures treated with soluble MUC-1 peptide. See also Agrawal et al., *J. Immunol., supra.*

Agrawal et al. reported that a relatively low percentage of stimulated T-cells were $CD69^+$. However, $CD69^+$, previously recognized as an early activation marker on T-cells, has now been shown to correlate with antigen stimulation. Gibbons, et al. 1996. *Cytometry.* 23:260–261. It was shown that PHA stimulated T-cells exhibit high CD69 expression at 30 minutes and the CD69 expression is apparent until 3–4 days of culture. In contrast to the PHA response, in antigen stimulated T-cells, CD69 is not expressed at early time periods (1 hour–3 days), whereas high CD69 expression was found on T-cell surfaces after approximately 6 days of in vitro culture. It was found that in MUC-1 antigen specific T-cells, CD69 expression at 6 days after stimulation correlated with expression of CD8 and CD4 on these T-cells.

The present studies demonstrate the generation of a mixed population of antigen-specific T-cells, some of which are CD4+ and some of which are CD8+. Because the proliferative response was blocked by both anti-CD4 and anti-CD8 antibodies, this suggests that both CD4+ and CD8+ T-cells are responding to antigen stimulation. The skilled artisan will recognize that in general, both CD4+ (T-helper) and CD8+ (T-cytotoxic) T-cells are necessary to generate an effective protective response against a pathogen, i.e., in conferring immunity against a tumor. However, the skilled artisan will also recognize that certain CD4+ T-cells are effective against pathogens, without the assistance of a CD8+ T-cell.

There are two types of CD4+ T helper cells. Type 1 CD4+ cells produce cytokines which assist in the CD8+ T-cell response (cytotoxic response). Type 2 CD4+ T-cells help B cells to produce antibodies. Depending on the nature of the pathogens, Type 1 or Type 2 CD4+ T-cells are required. however, some CD4+ T-cells themselves are cytotoxic and can produce the effector function.

E. In vitro Cytotoxic Responses of T-cells Stimulated with APCs Incubated with MUC-1 Peptide (BLP-25)-containing Liposomes Using the foregoing methods, the cytptoxic activity of T-cells stimulated with autologous APCs pulsed with liposomal BLP-25 was determined. The source of T-cells was PBLs from three $HLA.A2^+$ donors. Target T2 cells (HLA.A2⁺) were loaded with (SEQ ID NO: 1) nine-mer peptides (STAPPAHGV (SEQ ID NO: 2), SAPDTRPAP) which are contained within the peptide sequence of BLP-25. It was observed that loading with STAPPAHGV led to a higher upregulation of HLA.A2 expression on T2 cells than did (SEQ ID NO: 2) SAPDTRPAP (FIG. 6A).

Among the three donors, T-cells stimulated with liposomal BLP-25 had the ability to lyse T2 targets at various effector:target ratios (FIG. 6B). The negative control was and 8-mer ovalbumin (OVA) peptide (SEQ ID NO: 3) (SIINFEKL), which strongly upregulates HLA.A2 expression on T2 cells (FIG. 6A). Further, the addition of pan anti-class I HLA MAb (W6/32), but not the isotype control antibody (IgG$_1$), reduced the specific killing of (SEQ ID NO: 1) STAPPAHGV-loaded T2 cells (FIG. 6C). These data confirm that the present methods can be used to generate specific, biologically relevant T-cell responses, such as cytotoxicity.

Example 2

This example provides an illustrative technique for determining identifying smaller antigenic portions of T-cell antigens. As discussed above, smaller antigens have the benefit of a more directed T-cell response and more economic production. These methods basically involve isolating class I or class II molecules from cells and determining which portions of the processed antigen are presented to T-cells. Once the structures of these processed antigens are determined, they can form the basis for further refinement of a T-cell epitope.

1. Materials and Methods

Chemicals. Goat anti-mouse IgG$_{2b}$-Horse Radish Peroxidase (GαM-IgG$_{2b}$HRPO) was purchased from Southern Biotechnology Associates Inc. (Birmingham, Ala.), and used according to the manufacturer's specifications. Streptavidin-HRPO, H$_2$O$_2$ substrate and ABTS chromogen were obtained as a kit from Kirkegaard & Perry Laboratories Inc. (Gaithersburg, Md.). Maxisorb microtiter plates were from NUNC (Roskilde, Denmark).

NP40, aprotinin, leupeptin were from Sigma Chemical Co. (St. Louis, Mo.), iodoacetamide was obtained from Merck (Frankfurter Strasse, Darmstadt), PMSF from Boehringer Mannheim (Laval, Quebec, Canada). CNBr-Sepharose and Sepharose 4b were purchased from Pharmacia LKB Biotechnology AB (Uppsala, Sweden), Diethanolamine from Fisher Scientific (Fair Lawn, N.J.). All other chemicals were purchased from BDH (Toronto, Ontario, Canada).

Isolation of HLA class I from carcinoma cell lines. Approximately 2–3×10⁹ cells of each carcinoma cell line were grown in roller bottles. After a PBS wash, the cells were lysed in the roller bottles by rotating them for 45 min at 2–8° C. with 10 ml of lysis buffer (PBS containing 1 mg/ml NaN$_3$, 1% NP40, 10 μg/ml of leupeptin and aprotonin, 1 mM PMSF, and 1.8 mg/ml iodoacetamide). Lysates were pooled and spun at 3600 g for 15 min, the supernatant was then spun at 100,000 g at 28° C. for 45 min. The clarified lysate was stored frozen, at −20° C. until further use. DAUDI (non adherent) was grown in spinner flasks; the cells were collected by centrifugation, washed with PBS, and detergent extracted with the lysis buffer as described above.

Methods for the isolation of HLA class I were adapted from the methods of Mesher and colleagues. Mesher et al., Methods in Enzymology 92:86 (1983). HLA class I specific affinity columns (W6/32 and MA2.1) were prepared by coupling 10 mg of monoclonal antibody to 5 ml of swollen CNBr-Sepharose, following the manufacturer's specifications. A Sepharose 4b precolumn was coupled in tandem with the HLA class I specific affinity column, equilibrated with column wash buffer (PBS containing 1 mg/ml NaN$_3$, and 0.1% NP40), pre-eluted with the elution buffer (50 mM Diethanolamine with 0.1% NP40, 0.15 M NaCl pH 11.0) then re-equilibrated in the column wash buffer. For CAPAN-1, the HLA.A2 specific MAb BB7.2 was used in tandem with a W6/32 column.

The lysate was thawed, and loaded through the columns at 0.3 ml/min. After disconnecting the pre-column, the affinity columns were extensively washed with column wash buffer, then individually eluted with the elution buffer; 1 ml fractions were collected, and immediately neutralized with 1 M Tris/HCl, untitrated. The HLA class I activity in the fractions was monitored by a two-site ELISA assay, generally using the same antibody as the affinity column as the solid phase catcher, and biotinylated 9H1 (anti-β2-microglobulin) or biotinylated W6/32 (where appropriate, monomorphic anti-HLA class I-A,B,C) as the detector. Class I-reactive fractions by ELISA were pooled, brought to a final concentration of 1 mM PMSF, and frozen until further use.

Isolation and identification of MUC-1 peptides from the affinity purified HLA class I material from carcinoma cell lines. Methods used varied slightly from cell line to cell line, as described below. In general the affinity purified HLA class I material was thawed and acidified to pH 1 to 2 with 10% trifluoroacetic acid (TFA), then filtered through 0.45μ followed by 0.22μ to remove precipitate. In some cases, a Centricon 3 (Millipore, Marlborough, Mass.) filter (cut off 3000 daltons) was used to remove any high molecular weight proteins from the acid eluate. The released peptides were separated by Reverse Phase HPLC, on a Zorbax C8 column, 4.6×250 mm, on a Waters 600E HPLC with a Waters 996DA detector (Millipore Corp., Milford, Mass.). The sample was loaded in the mobile phase (0.05% TFA), and eluted with a gradient of 0–60% acetonitrile in the same mobile phase, over 30 min, at a flow rate of 1 ml/min. 1 ml fractions were collected and tested for MUC-1 activity in a direct ELISA by coating the fractions at a 1/10 dilution on microtiter wells (diluted to contain<15% acetonitrile), overnight.

Fraction coated wells were probed with 20 ng/well BCP8 monoclonal antibody, in ELISA diluent. BCP8 positive fractions were detected by GαM IgG$_{2b}$ HRPO (Southern Biotech). These were pooled, freeze-dried, and resuspended in a small volume of 0.05% TFA prior to secondary RP-HPLC. Secondary HPLC was either a repeat of the primary HPLC, or used a narrow bore Hypersil C18 column equilibrated in 0.1% Hexafluoroacetone (HFA) pH 8.1 in H$_2$O, gradient from 0 to 100% acetonitrile over 50 min, in the same modifier, at a flow rate of 200 μl/min. Nijman et al., J. Immunol 23:1215 (1993); Henderson et al., Proc. Natl. Acad. Sci. U.S.A. 90:10275 (1983). Fractions were again tested for BCP8 activity in direct ELISA, pooled and freeze dried, as described above.

The secondary RP-HPLC (pooled fractions) were affinity purified in solution with the BCP8 monoclonal antibody. Freeze dried pooled fractions were resuspended in a small volume of PBS. The material was tumbled overnight at 2–8° C. with 250–300 μg of to BCP8. The BCP8 and the bound peptides were separated from the free peptides on a 1 ml column of Protein G-Sepharose, then eluted with 8% acetic acid, pH 2. The protein G eluted fractions were re-chromatographed using the Zorbax C8 column as per the secondary RP-HPLC. BCP8 reactive fractions by ELISA were analyzed by electro spray mass spectrometry.

Mass spectral analysis and sequencing of peptides. Mass spectral analyses of eluted fractions were carried out on a Micromass VG Quattro triple quadrupole mass spectrometer with an electrospray ionization (ESI) source operating in positive ion mode.

Mass spectral sequencing. Sequencing of the peptide fragments was carried out in Sciex electrospray triple quadrupole mass spectrometer fitted with a collision cell in the second quadrupole. The sequence characteristics of these fragments were examined through collision activated disintegration in a collision cell and sequences were computed from the daughter ions, analyzed in the third quadrupole.

Competitive inhibition of binding of MAb BCP8 to class I MHC isolated putative MUC-1 peptide motifs by synthetic MUC-1 peptides. To show the specificity of binding of the BCP8 antibody to the peptides isolated from MCF-7, a fraction eluting at 19 min after secondary HPLC was diluted ⅙ with PBS and coated on microtiter wells overnight, then blocked as described above. The wells were incubated with 2 ng of BCP8 in 100 μl ELISA diluent, containing also amounts of peptide varying from 0–10 μM. Peptides used in this experiment were the 9 mers (SEQ ID NO: 3), SAPDTRPAP and GVTSAPDTR (SEQ ID NO: 17), and the 16 mer (SEQ ID NO: 15) GVTSAPDTRPAPGSTA. The ELISA was then processed as described above.

Confirmation of MAb BCP8 peptide specificity on peptide coated solid phases. Synthetic peptides were coated on microtiter plates at 0–4000 nmoles/well in 100 μl PBS containing 1 mg/ml NaN$_3$, overnight. A direct ELISA was performed as described above, except 50 ng/well of BCP8 antibody was used.

T2 cell culture. The T2 mutant cell line was kindly provided by Dr. Kevin Kane, Department of Immunology, University of Alberta, Edmonton, Canada. The T2 cell line was cultured in RPMI 1640 with 5% FBS, 1% Nutridoma-HU (Boehringer-Mannheim, San Diego, Calif.), 1% L-glutamine.

Synthetic Peptides. The following synthetic peptides were used in these experiments: MUC-1 peptides were sliding sequences from the MUC-1 tandem repeat (Table III): 9 mers: (SEQ ID NO: 15) GVTSAPDTR, (SEQ ID NO: 18) VTSAPDTRP, (SEQ ID NO: 18) TSAPDTRPA, (SEQ ID NO: 2) SAPDTRPAP, (SEQ ID NO: 19) APDTRPAPG, (SEQ ID NO: 20) PDTRPAPGS; 10 mers (SEQ ID NO: 26): GVTSAPDTRP, (SEQ ID NO: 27) VTSAPDTRPA, (SEQ ID NO: 28) TSAPDTRPAP, (SEQ ID NO: 30) SAPDTRPAPG, APDTRPAPGS, PDTRPAPGST; 7 mer (SEQ ID NO: 16) TSAPDTR; Positive control peptide (from influenza virus): FLPSDYFPSV (SEQ ID NO: 4) and from ovalbumin (SEQ ID NO: 3) SIINFEKL. Human MUC-1 25 amino acid peptide (SEQ ID NO: 5) STAPPAHGVTSAPDTRPAPGSTAPP, and its lipopeptide derivative containing palmitoyl group at the carboxy terminal lysine residue, as described above. Various synthetic peptides were prepared by automated solid phase synthesis with Fmoc amino acids using Milligen/Bioresearch Model 9500 peptide synthesizer (Millipore, Marlborough, Mass.). The peptides (SEQ ID NO: 2)5 were >95% pure as determined by HPLC.

TABLE III

MUCI synthetic peptides used in the T2 cell assay and their position in the MUCI tandem repeat

|  |  | % Change[a] in mean channel intensity |
|---|---|---|
| MUC1 tandem repeat (SEQ ID NO: 10) | G V T S A P D T R P A P G S T A P P A H |  |
| 9 mers | G V T S A P D T R (SEQ ID NO: 10) | 12 |
|  | V T S A P D T R P (SEQ ID NO: 17) | 29 |
|  | T S A P D T R P A (SEQ ID NO: 18) | 256 |
|  | S A P D T R P A (SEQ ID NO: 2) | 48 |
|  | A P D T R P A P G (SEQ ID NO: 19) | 66 |
|  | P D T R P A P G S (SEQ ID NO: 20) | 3 |
|  | D T R P A P G S T (SEQ ID NO: 21) | 52 |

[a]% Change in mean channel intensity of positive control (SEQ ID NO: 4) (FLPSDYFPSV) was 428.

T2 feeding experiment and FACS analysis. Prior to the peptide feeding experiments, the T2 cells were spun down and resuspended in RPMI 1640 with 1% Nutridoma, 1% L-glutamine, and 0, 5, 10 or 20 μg/ml β2-microglobulin. Cells were plated in microliter plates at 3×10$^5$ cells/well with 0–160 μmoles of peptide overnight at 37° C. and 7% CO$_2$. The cells were then stained with 0.5 μg/well of MA2.1 or an IgG$_1$, negative control. Bound MA2.1 monoclonal antibody was detected by incubation with GαM IgG$_1$, FITC. Fluorescence was measured at 488 nm on a FACSort (Becton-Dickinson, Mountain View, Calif.) flow cytometer within 5 days.

Liposomal Antigens. Liposomal antigen was formulated using a lipopeptide derivative of the human MUC-1 25 amino acid peptide STAPPAHGVTSAPDTRPAPGSTAPP. The lipid carrier consisted of dipalmitoyl phosphatidyl choline (DPPC), cholesterol (Chol) and dimyristoyl phosphatidyl glycerol (DMPG) (Genzyme, Cambridge, Mass.), Monophosphoryl lipid A (MPLA) (Ribi Immunochem Research Inc., Hamilton, Mont.) was included in the lipid mixture as an adjuvant.

Liposomal Antigens. Liposomal antigen was formulated using a lipopeptide derivative of the human MUC-1 25 amino acid peptide (SEQ ID NO: 5) STAPPAHGVTSAPDTRPAPGSTAPP. The lipid carrier consisted of dipalmitoyl phosphatidyl choline (DPPC), cholesterol (Chol) and dimyristoyl phosphatidyl glycerol (DMPG) (Genzyme, Cambridge, Mass.), Monophosphoryl lipid A (MPLA) (Ribi Immunochem Research Inc., Hamilton, Mont.) was included in the lipid mixture as an adjuvant.

T-cell culture in bulk. T-cell culture was as described above in Example 1.

Cytotoxic T lymphocyte assays. For the CTL assay, three (HLA.A2$^+$) normal donors' PBLs were used. The T-cells were grown for two weeks in bulk cultures as described above. At the end of two weeks, live T-cells were harvested from flasks and counted. T2 cells used as CTL targets were loaded overnight with various MUC-1 synthetic peptides at 200 μM in presence of exogenous β2m. Houbiers et al., Eur. J. Immunol 23:2072–2077 (1993); Stauss et al., Proc. Natl. Acad. Sci. U.S.A. 89:7871–7875 (1992). These peptide loaded T2 target cells were then loaded with $^{51}$Cr (using NaCrO$_4$) for 90 min and washed extensively. CTL assays were performed as previously described. Agrawal et al., supra. Percent specific killing was calculated as: experimental release—spontaneous release/maximum release—spontaneous release×100. The effector versus target ratio was used as (1, 10, 50, 100 and 150). Each group was set up in four replicate and mean percent specific killing was calculated. As negative control OVA peptide SIINFEKL loaded target T2 cells were used in the cytotoxic assay and percent specific killing of SIINFEKL loaded targets was subtracted from each data point to obtain MUC-1 peptide specific percent specific killing.

2. Results

A. MHC Class I Associated Peptides Isolated from MUC-1+ Tumor Cell Lines

After the W6/32 affinity purification of class I MHC molecules from MCF-7 cells, the peptides in the W6/32 positive peak were freed by acidification and separated by RP-HPLC. A typical chromatogram measured at 210 nm showed strong reactivity with the BCP8 antibody in the fractions eluting 18–23 min (FIG. 7). No reactivity was noted with a negative control antibody B195.3. Liu et al., Glycoconjugate Journal 12:607–617 (1995); Reddish et al., Glycoconjugate Journal 13: 1–12 (1996). Fractions 18–23 were rechromatographed on a Zorbax C8 column under the same conditions, resulting in a much cleaner chromatogram with a visible peak at 17 to 17.5 min with strong BCP8 reactivity in fractions eluting at 16.5 to 17.5 min (FIG. 8). The slightly different elution profile of the second HPLC is due to the use of a slightly different gradient elution in the second HPLC (See Materials and Methods). Once again, no reactivity was noted with the negative control MAb B195.3.

Mass spectral analysis of peptide pools from the BCP8 reactive fractions showed a great deal of variation both in length and number of peptides. It appears from the molecular weights that these peptides range between 5 to 20 amino acids in length with a majority of them falling between 10 to 20 amino acids in length. The specificity of MAb BCP8 for eluted class I associated MUC-1 peptides was tested. Anti-MUC-1 MAb BCP8 (Xing et al., Cancer Res. 52:2310–7 (1992)) was shown in a recent ISOBM workshop (M. R. Price et al., Summary Report on the ISOBM TD-4 Workshop: Analysis of 56 Monoclonal Antibodies Against MUC-1 Mucin, Tumor Biology 19:1–20 (1998)) to react with the minimal epitope (SEQ ID NO: 32) PDTRPA. FIG. 9 demonstrates that the two synthetic peptides containing the minimal epitope (SEQ ID NO: 32) PDTRPA inhibited binding of BCP8 to the isolated MUC-1 peptides (SEQ ID NO: 17) while the synthetic peptide GVTSAPDTR did not inhibit binding.

In a second approach, the W6/32 positive material from MCF-7 was acid treated, then neutralized and affinity purified with BCP8. In the A280 peak fractions, obtained after elution from a Protein G column, the affinity purified peptides were freed from the antibody by acidification, and separated on the Zorbax C8 RP-HPLC column as described above. The fractions eluting at 17–18 min had strong BCP8 reactivity and were subjected to mass spectral analysis and sequencing.

The mass spectrum (FIG. 10) showed three prominent fragments which appear to be degradation products of a larger peptide of at least 7 amino acids in length. Though the length of this sequence, which probably starts with TSA, remains ambiguous, the two tripeptide fragments, H+. (TSA) and H+. (DTR) indicate that they constitute the N-terminal and C-terminal fragments of a seven amino acid sequence of the MUC-1 tandem repeat, respectively. The presence of fragment H+. (TSAPDT) and (SEQ ID NO: 33) the absence of any other fragment beyond arginine lead to the conclusion that the peptide may either be a 7 mer (TSAPDTR) or a longer peptide.

The protocol for CAPAN-1 (HLA.A2) was to perform sequential affinity purifications of class I molecules using W6/32 followed by the HLA2.1 specific MAb, MA2.2. The acid eluted peptides were then spun through a 3000 dalton Centricon 3 spin filter to eliminate possible higher molecular weight contaminants. This peptide eluate was subjected to RP-HPLC on the Zorbax C8 column which also revealed a single peak of MAb BCP8 detected MUC-1 peptide reactivity, again at 17–18 min.

B. MUC-1 Negative Control Cells

Daudi cells were shown (by FACS analysis) to be negative for MUC1 expression, but positive for HLA class I heavy chain (W6/32 anti-HLA class I A, B, C) and light chain (9H1 anti-human β2-microglobulin). They were processed identically to the CAPAN-1 cell line, except for the modifications due to their non adherent growth pattern. After affinity purification with W6/32, acidification, followed by size exclusion (Centricon 3 spin), and RP-HPLC of the filtrate on the Zorbax C8 column, no significant reactivity with BCP8 was observed.

C. Upregulation of HLA.A2 Expression on T2 Mutant Cell Surface by MUC-1 Derived Synthetic Peptides In checker board experiments, the optimum concentration of β2-microglobulin for class I upregulation on T2 cells was determined to be 20 µg/ml (in agreement with Nijman et al., Eur. J. Immunol 23:1215 (1993)) and the amount of peptide was optimized as 20 µmoles/well (results not shown). Based on the finding of the MUC-1 7 mer (SEQ ID NO: 16) TSAPDTR MHC class I associated peptide sequence by electro spray mass spec (FIG. 10), we examined whether synthetic (SEQ ID NO: 16) TSAPDTR peptide can upregulate HLA.A2 expression on T2 cells. The TSAPDTR (SEQ ID NO: 16) synthetic peptide was used in excess at 50 µM/well along with other conditions similar for other 9 and 10 mer peptides. The 7 mer peptide (SEQ ID NO: 16) TSAPDTR did not significantly upregulate the expression of HLA.A2 on T2 cell surface (δMCI=2, data not shown). We then determined whether the (SEQ ID NO: 8) TSAPDTRPA 9 mer would upregulate class I expression on T2 cells. FIG. 11 shows that the TSA 9 mer caused strong upregulation of class I expression. Repeat experiments confirmed strong upregulation of class I expression on T2 cells by the TSA 9 mer which is stronger than the upregulation of class I expression by other MUCI 9 mers (Table III).

D. In vitro Cytotoxic T Lymphocyte Response

We performed in vitro CTL assays in order to determine whether the MUC-1 peptides shown to be capable of binding to HLA.A2 on T2 mutant cells can be recognized as CTL epitopes in the context of MHC class I HLA.A2 molecules on target cells. T-cells from PBLs of three HLA.A2+ donors were primed in vitro against MUC-1 antigen using a lipopeptide derivative of 25 amino acid MUC-1 peptide encapsulated in liposome pulsed autologous PBLs as APCs. The stimulated T-cells were harvested following two weeks in vitro culture (with 2 weekly restimulations) and tested for their cytotoxic activity against MUC-1 derived synthetic peptide (9 mers and 7 mer) loaded T2 cells as target in a 5 h $^{51}$Cr release assay (FIG. 6). Among the seven MUC-1 derived synthetic peptides tested, targets loaded with 9 mers TSA . . . and SAP . . . peptides were specifically killed to the highest degree by the same 2 donors. The targets loaded with 7 mer TSA . . . peptide were weakly killed by donor 2 at higher E/T ratios. Other peptide loaded T2 targets showed a low to intermediate degree of specific killing.

What is claimed is:

1. A MUC-1 peptide that is covalently modified with a lipid moiety, wherein said MUC-1 peptide generates an antigen-specific T-cell response and comprises a sequence of from about 7 to about 20 amino acids of the sequence STAPPAHGVTSAPDTRAPGSTAPP (SEQ ID NO. 5).

2. A lipid-modified MUC-1 peptide according to claim 1, which has an amino acid sequence that consists of one to three copies of a 7–20 amino acid long peptide obtained from the peptide STAPPAHGVTSAPDTRPAPGSTAPP (SEQ ID NO: 5).

3. A lipid-modified MUC-1 peptide according to claim 2, which has an amino acid sequence that consists of from one to three copies of the peptide STAPPAHGVTSAPDTRPAPGSTAPP (SEQ ID NO: 5).

4. A lipid-modified MUC-1 derivative according to claim 3, which is BLP-25.

5. A lipid-modified MUC-1 derivative according to claim 1, wherein said lipid contains a monounsaturated or polyunsaturated fatty acyl group.

6. A lipid-modified MUC-1 derivative according to claim 1, wherein said lipid is selected from the group consisting of palmitoyl, myristoyl, stearoyl and decanoyl moieties.

7. A composition, comprising a liposomally associated a lipid-modified MUC-1 derivative according to claim 1.

8. A composition according to claim 7, where in said lipid-modified MUC-1 peptide has an amino acid sequence that consists of one to three copies of a 7–20 amino acid long peptide obtained from the peptide STAPPAHGVTSAPDTRPAPGSTAPP (SEQ ID NO: 5).

9. A composition according to claim 8, wherein said lipid-modified MUC-1 peptide has an amino acid sequence that consists of from one to three copies of the peptide STAPPAHGVTSAPDTRPAPGSTAPP (SEQ ID NO: 5).

10. A composition according to claim 9, wherein said lipid-modified MUC-1 derivative is BLP-25.

11. A composition according to claim 7, wherein said lipid contains a monounsaturated or polyunsaturated fatty acyl group.

12. A composition according to claim 11, wherein said lipid is selected from the group consisting of palmitoyl, myristoyl, stearoyl and decanoyl moieties.

13. A composition according to claim 12, wherein said lipid is a palmitoyl moeity.

14. A composition according to claim 7, wherein said liposome is a multilamellar liposome.

15. A composition according to claim 13, wherein said liposome is a multilamellar liposome.

16. A MUC-1 peptide that is covalently modified with a lipid moiety, wherein said MUC-1 peptide generates an antigen-specific T-cell response and consists essentially of a sequence of from about 7 to about 20 amino acids of the sequence TAPPAHGVTSAPDTRAPGSTAPP (SEQ ID NO. 23).

\* \* \* \* \*

UNITED STATES PATENT AND TRADEMARK OFFICE
CERTIFICATE OF CORRECTION

PATENT NO.        : 6,600,012 B1
APPLICATION NO.   : 09/497232
DATED             : July 29, 2003
INVENTOR(S)       : Agrawal et al.

It is certified that error appears in the above-identified patent and that said Letters Patent is hereby corrected as shown below:

At Column 45, line 23, Claim 1, replace -- STAPPAHGVTSAPDTRAPGSTAPP (SEQ ID NO. 5) -- with -- STAPPAHGVTSAPDTRPAPGSTAPP (SEQ ID NO. 5) --.

Signed and Sealed this

Twenty-eighth Day of September, 2010

David J. Kappos
*Director of the United States Patent and Trademark Office*